(12) United States Patent
Hasegawa et al.

(10) Patent No.: US 7,972,840 B2
(45) Date of Patent: Jul. 5, 2011

(54) APPARATUS FOR CULTURING ORGANISM AND METHOD OF CULTURING ORGANISM

(75) Inventors: Ryou Hasegawa, Izumisano (JP); Daisuke Suzumura, Izumisano (JP)

(73) Assignee: Phytoculture Control Co., Ltd., Izumisano-Shi (JP)

( * ) Notice: Subject to any disclaimer, the term of this patent is extended or adjusted under 35 U.S.C. 154(b) by 736 days.

(21) Appl. No.: 10/495,534

(22) PCT Filed: Nov. 15, 2002

(86) PCT No.: PCT/JP02/11906
§ 371 (c)(1),
(2), (4) Date: May 13, 2004

(87) PCT Pub. No.: WO03/042352
PCT Pub. Date: May 22, 2003

(65) Prior Publication Data
US 2005/0032206 A1    Feb. 10, 2005

(30) Foreign Application Priority Data

Nov. 16, 2001  (JP) .................... 2001-351680

(51) Int. Cl.
*C12M 1/12*    (2006.01)
*A01G 31/00*   (2006.01)
*A01G 25/00*   (2006.01)
(52) U.S. Cl. .......... 435/297.1; 47/60; 47/64; 47/80
(58) Field of Classification Search ............. 435/297.1; 47/64, 80, 60
See application file for complete search history.

(56) References Cited

U.S. PATENT DOCUMENTS

| | | | | |
|---|---|---|---|---|
| 4,289,854 A | * | 9/1981 | Tolbert et al. | 435/394 |
| 4,829,002 A | * | 5/1989 | Pattillo et al. | 435/297.1 |
| 5,180,676 A | * | 1/1993 | Ichikawa et al. | 435/383 |
| 6,200,809 B1 | | 3/2001 | Klimaszewska et al. | |

(Continued)

FOREIGN PATENT DOCUMENTS
JP    02-195827 A    8/1990
(Continued)

OTHER PUBLICATIONS

Adelberg et al., Scientia Horticulturae, "Micropropagation, decontamination, trancontinental shipping and hydroponic growth of Cattleya while sealed in semipermeable membrane vessels", vol. 73, pp. 23-35, (1998).

(Continued)

*Primary Examiner* — Walter D Griffin
*Assistant Examiner* — Lydia Edwards
(74) *Attorney, Agent, or Firm* — Birch, Stewart, Kolasch & Birch, LLP

(57) ABSTRACT

There are provided an organism-culture apparatus in which a pooled culture medium and a culturing tissue is not directly contacted, which comprises a culture medium, and a microporous body having the water-absorbing ability, a part of which is immersed in the culture medium, or an intervening body connected to the microporous body which can supply the culture medium to the microporous body by contact between a part of the intervening body and the culture medium, wherein the culture medium is transferred upwardly via communicating pores in the interior of the microporous body to supply the culture medium to an organism tissue or an organism cell placed on a surface of the microporous body, whereby, the organism tissue or the organism cell is cultured, as well as a method of culturing an organism using the same.

13 Claims, 26 Drawing Sheets

U.S. PATENT DOCUMENTS

| | | | |
|---|---|---|---|
| 6,314,678 B1* | 11/2001 | Akai | 47/80 |
| 6,455,310 B1* | 9/2002 | Barbera-Guillem | 435/383 |
| 2002/0164798 A1* | 11/2002 | Eudes et al. | 435/424 |

FOREIGN PATENT DOCUMENTS

| | | | |
|---|---|---|---|
| JP | 03-37835 A | | 4/1991 |
| JP | 3-160988 A | | 7/1991 |
| JP | 09-191785 A | | 7/1997 |
| JP | 10-328283 A | | 12/1998 |
| JP | 2000-23658 A | | 1/2000 |
| JP | 2000324951 | * | 11/2000 |
| JP | 2001-045895 A | | 2/2001 |
| SU | 901266 | | 1/1982 |
| SU | 948998 | | 8/1982 |
| SU | 1585325 A1 | | 8/1990 |
| WO | WO-87/07113 A | | 12/1987 |

OTHER PUBLICATIONS

"A Manual for the Practical Study of the Root-Nodule Bacteria" by J.M. Vincent, IBP Handbook No. 15, Blackwell Scientific Publications Oxford and Edinburgh.

"Ethylene-mediated phenotypic plasticity in root nodule development on *Sesbania rostrata*", by Manuel Fernandez-Lopez, et al., Proc. Natl. Acad. Sci., USA, vol. 95, pp. 12724-12728, Oct. 1998.

Studies of Eucalypt Mycorrhizas, I, A Method of Mycorrhiza Induction in *Eucalyptus gummifera* (Gaertn. & Hochr.) by *Pisolithus tinctorius* (Pers.) Coker & Couch., by K.J. Mullette, Aust. J. Bot., 1976, 24, pp. 193-200.

"The preparation in vitro of chrysanthemum for transplantation to soil," by Andrew V. Roberts, et al., Plant Cell Tissue and Organ Culture 21: 129-132, 1990.

"Seed Germination Sucess Experiment", by Barbieri et al., http://biology.csub.edu/germinat.htm., May 23, 1997.

"Pre-infection events in non-nodulating species of African Acacia", L.A. Harrier, et al., 2000 East African Wild Life Society, Afr. Jr. Ecol. 38, pp. 8-15.

"Factors Affecting nod Gene Induction, Particularly in Rhizobia from Tropical Trees", John Edward Shaw, A thesis presented to the University of Dundee, Aug. 1993.

JP Final Rejection, Appl. No. 2003-544172, Nov. 2, 2010, pp. 1-3.

* cited by examiner

APPARATUS FOR CULTURING ORGANISM AND METHOD OF CULTURING ORGANISM

BACKGROUND OF THE INVENTION

The present invention relates to an apparatus and a method for culturing an organism tissue or an organism cell. More particularly, the present invention relates to an apparatus and a method for culturing an organism tissue or an organism cell, without directly contacting a pooled culture medium and an organism tissue or an organism cell, by supplying a culture medium to an organism tissue or an organism cell via a microporous body.

DESCRIPTION OF THE PRIOR ART

Due to rapid progression in the bio-technological field in recent years, organism tissue culture techniques have become significantly important, from a viewpoint at a level of a basic research investigating expression of a particular gene and metabolism of a particular factor, and at an industrial level such as propagation of a rare plant, enlargement of a genetic mutation, mass production of a useful substance, shortening of a culture period, preservation of a genetic source and the like.

SUMMARY OF THE INVENTION

However, of such tissue culture techniques, in the tissue culture using a solid medium such as an agar medium, it was necessary that the culturing tissue is subcultured to a fresh medium within a relatively short period, because water and nutrients in the culture medium are rapidly consumed by the culturing tissue while waste products are excreted from the culturing tissue into the culture medium. In addition, the culture medium is contaminated in some cases upon such the subculture operation. In such the case, there was a problem that the culturing tissue can not be easily isolated from the tissue culture system again in a conventional tissue culture system in which the culturing tissue and the culture medium are directly contacted. Furthermore, in viable cell counting, the number of viable cells such as of bacteria in a sample is counted by measuring the number of colonies on an agar plate medium. But, this can not be conducted in the case of bacteria such as lactic acid bacteria and the like because such bacteria have an extremely acidic growth pH range and, therefore, the medium can not be solidified to prepare an agar plate medium under such the condition due to nature of an agar.

In addition, microorganisms have been found which live under a severe environment such as high pressure, low pressure, strong acidic, strong alkalic, high temperature, low temperature, high salt concentration, anaerobic, aerobic conditions, radiation, an organic solvent and the like (barophilic, acidophilic, alkaliphilic, thermophilic, psychrophilic, highly halophihc, solvent-resistant, radiation-resistant bacteria and the like), and it has been known that they produce a useful substance such as an enzyme and the like which can effectively act even under such the severe environmental conditions. Therefore, it is expected that such the useful substance is isolated by culturing these microorganisms to industrially utilize in a variety of uses, and there is a need for a culturing apparatus and method which can be suitably used for culturing such microorganisms.

The present inventors studied intensively in view of the aforementioned problems and, as a result, found that the problems can be solved by supplying a culture medium to a culturing tissue via a particular microporous body, which resulted in completion of the present invention.

That is, in the first aspect, the present invention provides (1) an organism-culturing apparatus, which comprises a culture medium, a microporous body having the water-absorbing ability, a part of which is immersed in the culture medium, and a container containing at least a part of the culture medium and the microporous body, wherein the culture medium is transferred upwardly via communicating pores in the interior of the microporous body having the capillary attraction, to supply the culture medium to an organism tissue or an organism cell placed on a surface of the microporous body, whereby, the organism tissue or the organism cell is cultured.

In addition, in the second aspect, the present invention provides (2) the organism-culturing apparatus according to (1), wherein the microporous body has a shape of an upright cylindrical type or pillar type.

In addition, in the third aspect, the present invention provides (3) the organism-culturing apparatus according to (1) or (2), wherein the microporous body comprises a cylindrical or pillar type part, and a pan type part continuing upwardly from the cylindrical or pillar type part and having a greater outer diameter than that of the cylindrical or pillar type part, in which a center of the pan type part is recessed, wherein a part of the pan type part is projected in its diametric direction and has a greater outer diameter than that of an opening of a container, and the microporous body is supported by the container by contact between a bottom of the projected part and a periphery of an opening of the container.

In addition, in the fourth aspect, the present invention provides (4) the organism-culturing apparatus according to any one of (1) to (3), wherein the microporous body is a fired product of a non-metal inorganic solid material.

In addition, in the fifth aspect, the present invention provides (5) the organism-culturing apparatus according to any one of (1) to (3), wherein the microporous body is an open-cell type plastic foam.

In addition, in the sixth aspect, the present invention provides (6) an organism-culturing apparatus, which comprises a culture medium, a microporous body having the water-absorbing ability, an intervening body connected to the microporous body which can supply the culture medium to the microporous body by contact between a part of the intervening body and the culture medium, and a container containing at least a part of the culture medium and the microporous body, wherein the culture medium supplied via the intervening body is transferred upwardly via communicating pores in the interior of the microporous body having the capillary attraction, to supply the culture medium to an organism tissue or an organism cell placed on a surface of the microporous body, whereby, the organism tissue or the organism cell is cultured.

In addition, in the seventh aspect, the present invention provides (7) the organism-culturing apparatus according to any one of (1) to (6), wherein the organism tissue or the organism cell is a tissue or a cell of plants, fingi or bacteria.

In addition, in the eighth aspect, the present invention provides (8) a method of culturing an organism, which comprises transferring a culture medium upwardly via communicating pores in the interior of a microporous body having the water-absorbing ability, a part of which is immersed in the culture medium, to supply the culture medium to an organism tissue or an organism cell placed on a surface of the microporous body, whereby, the organism tissue or the organism cell is cultured.

In addition, in the ninth aspect, the present invention provides (9) the method of culturing an organism according to claim 8, wherein the organism tissue or the organism cell is a tissue or a cell of plants, fingi or bacteria.

Unless otherwise indicated herein, an organism body and an organism tissue such as of animals, plants, fingi, bacteria and the like are collectively referred to as an organism tissue. In addition, an individual cell prepared by an enzyme treatment of the tissue is referred to as an organism cell. In addition, a medium which contains a variety of medium ingredients such as nutrients, buffers, viscosity-adjusting agents, antibiotics, osmoregulatories, enzymes, natural materials (such as yeast extract), regulators (such as plant hormone), amino acids, vitamins and the like are referred to as a culture medium.

According to the first to ninth aspects of the present invention, consumption of the culture medium can be reduced because only a necessary amount of the culture medium is supplied to the organism tissue by the capillary action of the microporous body, as compared with the conventional culturing system in which the organism tissue is cultured by directly contacting it with the culture medium.

In addition, in the apparatus and method according to the present invention, a necessity of operations such as stirring and shaking is lowered because the organism tissue is cultured outside the pooled culture medium and on the microporous body such that a gas required for culturing the tissue such as oxygen is adequately supplied.

In addition, in the apparatus and the method according to the present invention, the number of required subcultures to be conducted can be reduced because the waste products which are excreted from and accumulated near the organism tissue are also diffused into the culture medium via the microporous body and diluted therein. Therefore, in the apparatus and the method of the present invention, together with the aforementioned effects, contamination which may be caused upon subculturing operation can be prevented, and culturing in one culture medium for a long period without subculture becomes possible.

In addition, even when contamination of the culture medium with microorganisms and the like is caused, the organism tissue is not contaminated, or at least, the time, until the organism tissue is contaminated, is extended because the culture medium is supplied to the organism tissue via the communicating pores and, thereby, the organism tissue can be transferred to the fresh medium, before it is contaminated, to prevent contamination of the organism tissue itself.

In addition, the plate agar culture which is not affected by the pH, temperature, high pressure, low pressure, ingredients of the culture medium, ultraviolet, radiation or the like becomes possible, and culture can be conducted by merely placing the microporous body which has been sterilized into the culture container and then pouring the culture medium therein without conducting procedures for melting or solidifying agar. Alternatively, the organism tissue can be easily cultured by aseptically transferring the microporous body impregnated with the culture medium to a clean bench such as by aseptically packaging it with a retort pouch or the like, opening it in the clean bench and placing it into the culture container.

In particular, according to the second aspect of the present invention, the cost for manufacturing the organism-culture apparatus can be reduced by utilizing the cylindrical or pillar type microporous body which can be easily formed.

In addition, according to the third aspect of the present invention, culture for a long period or culture a larger amount of the organism tissue become possible by utilizing a pan type microporous body having a larger diameter than that of the cylindrical or pillar type microporous body.

In addition, according to the fourth aspect of the present invention, the organism-culture apparatus having the excellent formability and durability and a light weight, can be provided by utilizing the fired product of a non-metal inorganic solid material as the microporous body.

In addition, according to the fifth aspect of the present invention, the organism-culture apparatus of the present invention can be applied to a variety of uses by utilizing the open-cell type plastic foam as the microporous body, because it has the excellent moldability, it can be formed to a variety of shapes and it can be prepared into a light microporous body.

In addition, the organism-culture apparatus of the present invention can be suitably applied to culture under an environment such as in a space station where a culturing area and a weight of the apparatus should be restricted, because the fired product of a non-metal inorganic solid material or open-cell type plastic foam as described above can be formed or molded smaller.

In addition, according to the sixth aspect of the present invention, the culture medium can be continuously supplied to the microporous body and the organism tissue even when the culture medium is consumed, the surface thereof is lowered and, thereby, it becomes possible to culture for a long period, because the culture medium is supplied to the microporous body and the organism tissue via the intervening body even when the microporous body is not directly contacted with the culture medium. In addition, from a viewpoint of a design of the culture apparatus, a degree of freedom in designing the container can be enhanced, because the flexibility of a relative location of the microporous body to the container is enhanced.

In addition, particularly, a metabolizing rate and a growing rate of a tissue or a cell of plants, fingi and bacteria are low relative to those of a tissue or a cell of animals. For this reason, it was impossible to culture the tissue or the cell of plants, fingi and bacteria in a single medium for a long period of time because a lifetime of the conventional medium such as an agar medium is shorter as compared with that of the culturing tissue or cell due to dryness of the medium. In addition, although culture can be continued for a long period in the liquid culture, in addition to necessity of shaking, there is a risk that it may give a stress due to a drastic change in the environment near the culturing tissue or cell and contamination may be caused upon exchanging the culture medium. According to the seventh aspect of the present invention, the organism tissue or cell can be cultured for an extremely long period without subculturing or repotting because the culture medium is successively supplied to the microporous body of the culture apparatus. Therefore, a culture apparatus can be provided by which a greater amount of a useful substance can be obtained more conveniently in a single culture operation, upon extraction of a useful substance from a tissue or a cell of plants, fingi and bacteria, and by which the conditioning operation can be conducted by merely exchanging the culture medium after redifferentiation, particularly in the case of culture a plant.

In addition, according to the eighth aspect of the present invention, an organism-culture apparatus having the aforementioned advantages can be provided.

Furthermore, particularly, a metabolizing rate and a growing rate of a tissue or a cell of plants, fingi and bacteria are lower as compared with those of a tissue or a cell of animals. For this reason, it was impossible to culture the tissue or the cell of plants, fingi and bacteria in a single medium for a long period of time because a lifetime of the conventional medium such as an agar medium is shorter as compared with that of the culturing tissue or cell due to dryness of the medium. In addition, although culturing can be continued for a long period of time in the liquid culture, in addition to necessity of shaking, there is a risk that it may give a stress due to a drastic change in the environment near the culturing cell and contamination may be caused upon exchanging the culture medium. According to the ninth aspect of the present invention, the organism tissue or cell can be cultured for an extremely long period without subculturing or repotting because the culture medium is successively supplied to the microporous body of the cultur apparatus. Therefore, a culture method can be provided by which a greater amount of a useful substance can be obtained more conveniently in a single culturing operation, upon extraction of a useful substance from a tissue or a cell of plants, fungi and bacteria, and by which the conditioning operation can be conducted by merely exchanging the culture medium after redifferentiate, particularly in the case of culturing a plant.

DETAILED DESCRIPTION OF THE PREFERRED EMBODIMENTS

Figure 1:
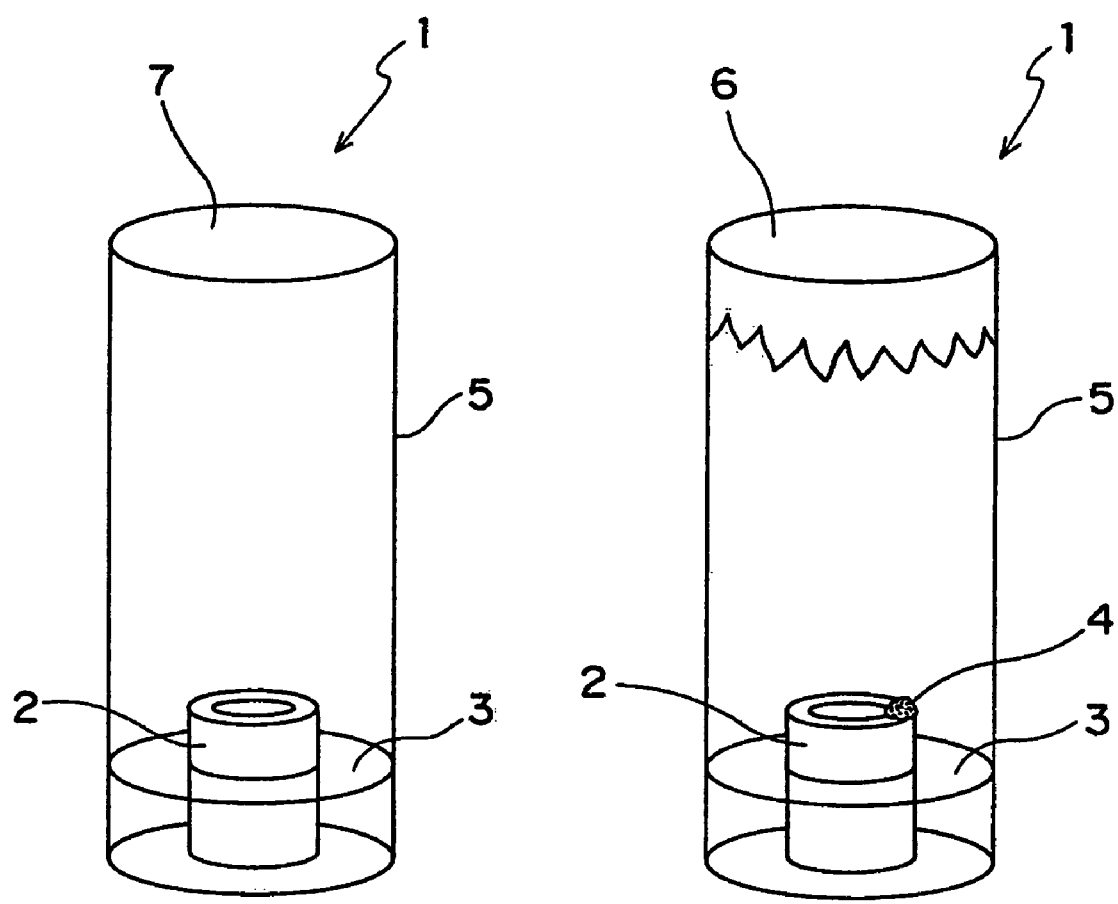
FIG. 1 is a perspective view from an upper visual point showing one embodiment of the culturing apparatus of the present invention.

Next, the embodiment of organism-culture apparatus of the present invention is described with referring to FIGS. 1-6.

Firstly, the first embodiment of an organism-culture apparatus of the present invention is an organism-culture apparatus comprising a culture medium 3 and a cylindrical or pillar type microporous body 2 which stands upright from a bottom of said organism-culture apparatus 1, which can propagate, dedifferentiate, differentiate, regenerate, preserve, select, isolate or cross an organism tissue or an organism cell 4 by placing it on a surface of said microporous body.

A culture medium 3 used in the organism-culture apparatus is not particularly limited, but any culture media may be used as far as they can propagate, dedifferentiate, differentiate and regenerate the organism tissue or the organism cell. Examples thereof include, for example, a culture medium for a plant tissue such as an MS (Murashige-Skoog) medium, a B5 medium, a W medium, an NT medium, a Kao8P medium, an LS medium, an H medium, a KC medium, an HB medium, WPM, a Kassanis medium, a Neelsen's medium, a Galzy medium, a Nitsh and Nitsh medium, a Noushi medium and the like to which a variety of plant hormones, amino acids, vitamins, antibiotics, osmoregulatories, buffering agents, natural materials (such as yeast extract), or enzymes may be added depending upon a purpose; a culture medium for an animal tissue such as a 199 medium, a minimum Eagle medium (MEM), a dulbecco modified minimum Eagle medium (DMEM), RPMI1640, a Ham's F12 medium, an MCDB 104 medium, an MCDB 153 medium, an ES medium, MEM1, DEMEM1, DEMEM2 and the like to which a variety of amino acid ingredients, vitamins, enzymes (such as trypsin), antibiotics, osmoregulatories, buffering agents, natural materials (such as yeast extract and serum) may be added depending upon a purpose; a culture medium for a fungus such as a modified Ohta medium, a Hamada's EBIOS-sucrose medium, an M medium, an MYP medium, a PDA medium, an Ohta medium, a Mozel b-medium, a Wessels and Niderpruem minimum medium for mating, a Kerruish and Da Costa medium, a Goodey and Lucetohole medium, a Czapek medium, an Yeast infusion medium, an Wickerham synthetic medium, an MY medium, an oatmeal medium, a modified Gorodkowa medium, a Christensen's urea medium, a Henneberg medium, a Czapek-Dox medium, a Uschinsky medium, a thioglycolate medium for anaerobic fingi, a Kleyn sodium acetate medium, an yeast complete synthetic medium (Wickerham), a succinate-nitrate medium, a Gorodkowa medium, a cornmeal medium, a nitrate medium, a Fowells sodium nitrate medium, a Lindegren medium and the like to which a variety of amino acids, vitamins, enzymes, antibiotics, osmoregulatories, buffering agents, natural materials (such as yeast extract) may be added depending upon a purpose; a culture media for a bacterium such as a potato sucrose medium, a BL medium, a CW medium, a modified CCFA medium, a B-CYEα medium, a WYOα medium, a DNase medium, a PS latex medium, a TCBS medium, a BGLB medium, an EC medium, a CVT agar, an EMB medium, a BCM O157 medium, an NAC agar, an OF medium base, a dextrose-phosphorate-peptone medium, a Rusell medium, a Kligler medium, a TSI medium, a SIM medium, a Simmons sodium citrate medium, a malonate medium, a urea medium, a Christensen urea medium, a lysine iron agar medium, a medium for testing lysine decarbonization, an LIM medium, an OIML medium, a VPOF medium, an SS medium, an SS-SB medium, a MacConkey medium, a DHL medium, a brilliant green medium, an XLD medium, a Rappaport broth, a Hajna tetrathionate broth base, a selenite broth base, an SBG sulfur broth base, a tetrathionate broth, an EEM broth, a heart infusion medium, a brain heart infusion medium, an SCD medium, an SCDLP medium, a BTB lactose medium, a Drigalski medium, an SCDLP broth, a lactose broth JP medium, a cowpat for methanogenic bacteria, an MS-1 (1.5% casamino acid, 0.01% cysteine, 0.01% tryptophan, 0.05% sodium citrate, 0.2% sodium succinate, 0.05% $K_2HPO_4$, 0.05% $KH_2PO_4$, 30.01% KNO, 2.0% $MgSO_4.7H_2O$, 0.005% $FeSO_4.7H_2O$, 22-26% NaCl), an MS-2 medium (0.5% casamino acid, 1.0% yeast extract, 0.5% peptone, 0.3% sodium citrate, 0.5% KCl, 2.0% $MgSO_4.7H_2O$, 0.005% $FeSO_4.7H_2O$, 25% NaCl) and an MS-3 medium (1.0% yeast extract, 0.5% $MgCl_2.6H_2O$, 0.5% $NH_4Cl$, 25% NaCl) for high halophilic bacteria, an MSA-4 medium (1.0% peptone, 0.3% sodium citrate, 2.0% $MgSO_4.7H_2O$, 0.2% KCl, 5.0% $NaCO_3.10H_2O$, 25% NaCl) for an alkaliphilic and high halophilic bacteria, a YSG medium for thermophilic and acidophilic bacteria, an MH-1 medium (1.0 g of yeast extract, 1.0 g of Tryptone, 30 g of NaCl, 3.5 g of $MgSO_4.7H_2O$, 2.8 g of $MgCl.6H_2O$, 0.2 g of $FeSO_4.7H_2O$, 0.33 g of KCl, 0.2 g of $NH_4Cl$, 50 mg of NaBr, 20 mg of $H_3BO_3$, 0.5 g of $KH_2PO_4$, 7.5 mg of $SrCl.6H_2O$, 10 mg of $(NH_4)_2SO_4$, 0.1 mg of $Na_2WO_4.2H_2O$, 50 mg of KI, 0.75 g of $CaCl.2H_2O$, 2 mg of $NiCl.6H_2O$, 1 mg of Resazurine, 10 ml of trace ingredients solution (1.5 g of nitriro triacetate, 3 g of $MgSO_4.7H_2O$, 0.5 g of $MnSO_4.7H_2O$, 1 g of NaCl, 0.18 g of $ZnSO_4.7H_2O$, 10 mg of $CuSO_4.5H_2O$, 20 mg of $KAl(SO_4)_2.7H_2O$, 10 mg of $H_3BO_3$, 10 mg of $Na_2MoO_2.2H_2O$, 25 mg of $NiCl_2.6H_2O$, 0.3 mg of $Na_2SeO_3.5H_2O$ per 1 L of distilled water), 25 g of Sulfer, 25 g of $Na_2S.9H_2O$ per 1 L of distilled water), an MH-2 medium (0.01% yeast extract, 0.01% casamino acid, 0.1% carbon source, 0.02% NaCl, 0.03% $KH_2PO_4$, 0.13% $(NH_4)_2SO_4$, 0.025% $MgSO_4.7H_2O$, 0.005% $CaCl_2.2H_2O$, glucose) and an MH-3 medium (5 g of Bacto Peptone, 1 g of Bacto Yeast Extract, 0.1 g of $FeC_5H_5O_7$, 19.45 g of NaCl, 5.9 g of $MgCl$, 3.24 g of $Na_2SO_4$, 1.8 g of $CaCl_2$, 0.55 g of KCl, 0.16 g of $NaHCO_3$, 0.08 g of KBr, 0.034 g of $SrCl_2$, 0.022 g of $H_3BO_3$, 0.004 g of sodium silicate, 0.0024 g of NaF, 0.0016 g of $NH_4NO_3$, 0.008 g of $Na_2HPO_4$, 10 g of casein or starch per 1 L of distilled water) for thermophilic archaebacteria.

Next, a microporous body 2 having the water-absorbing ability used in the organism-culture apparatus of the present invention is not particularly limited, but any microporous bodies may be used as far as they have the water-absorbing ability being capable of retaining 0.005-500 (wt/wt), preferably 0.01-100 (wt/wt), more preferably 0.025-50 (wt/wt), most preferably 0.05-5 (wt/wt)-fold amount of water at 20° C., and have communicating pores having a pore diameter of 0.02-900 μm, preferably 0.05-80 μm, more preferably 0.1-9 μm, most preferably 0.2-3 μm at a pore rate (vol/vol) of 0.05-1, preferably 0.2-0.4 relative to the microporous body. Like this, by adjusting a pore diameter and a pore rate in the microporous body, even when a culture medium is contaminated with virus, bacterium, filamentous fungus, algae or protozoa, those organisms can not reach an organism tissue being cultured or it takes a longer time for those organisms to reach there due to the filtering effect of the microporous body and, by transferring the organism tissue to another culture apparatus during that time, the organism tissue itself can be prevented from being contaminated.

In addition, preferably the microporous body has not only the aforementioned characteristics but also resistance to high temperature and high pressure sterilizing treatment such as treatment with an autoclave, and strong alkaline, strong acidic, high temperature, low temperature, organic solvent, radiation or gravity-applying conditions or the like, examples of the microporous body include porous bodies obtaining by kneading, forming and firing non-metal inorganic solid raw materials such as No. 10 clay, porcelain No. 2 clay (Shiroyama Cerapot) and Murakami clay (produced in Niigata Prefecture in Japan) according to the conventional method, as well as open-cell type plastic foam materials such as polyvinyl alcohol foam, polyurethane foam, polystyrene foam, vinyl chloride resin foam, polyethylene foam, polypropylene foam, phenol resin foam and urea resin foam. In particular, when non-metal inorganic solid raw materials are made into porous bodies which easily absorb and release water, it is preferable that those raw materials are fired while containing, for example, petalite and alumina at 50-60% by weight. Generally, the petalite preferably contains 76.81% by weight of $SiO_2$, 16.96% by weight of $Al_2O_3$, 4.03% by weight of $LiO_2$, 0.26% by weight of $K_2O$ and 1.94% by weight of inevitable impurities. In addition, non-metal inorganic raw materials may contain powdery inorganic foam. Further, the microporous body used in the organism-culture apparatus of the present invention is composed of a non-metal inorganic material, the strength of which is not substantially reduced or the shape of which is not transformed even when it has absorbed water.

As a method of forming a non-metal inorganic solid raw material, there are forming methods which are known in the art such as slip casting forming, extruding forming, press forming and potter's wheel forming. In particular, from a viewpoint of large scale production and reduction in the cost, extruding forming is preferable. In addition, drying after forming can be performed using the normal methods and conditions known in the art. Subsequent firing of a formed body is not particularly limited as far as firing is performed by the conventional conditions and methods. For example, oxidative firing by which a desired pore is easily obtained can be selected. A firing temperature is 1000° C. to 2000° C., preferably 1100° C. to 1500° C., more preferably 1150° C. to 1250° C., most preferably 1200° C. When a temperature for firing a non-metal inorganic solid raw material is lower than 1000° C., a sulfur component easily remains and, on the other hand, when the temperature is higher than 2000° C., the desired water-absorbing property is not obtained.

On the other hand, as a method of molding a microporous body composed of an open-cell type plastic foam, there are melt foaming molding, solid phase foaming molding and casting foaming molding.

Main steps in melt foaming molding comprise melting and kneading, molding of an unfoamed sheet, heat foaming or extrusion foaming, cooling, cutting and processing. In solid phase foaming molding, a polymer is foamed in the solid phase or in the state near the solid phase. In addition, in casting foaming molding, a liquid raw material (monomer or oligomer) is cast and foamed while reacting in the air. In order to foam an open-cell type plastic foam, a foaming agent is generally used.

In addition, a microporous body 2 has a shape of cylindrical type or pillar type, a shape including cylindrical type or pillar type part and a pan type part continuing upwardly from the cylindrical type or the pillar type and having a larger outer diameter than that of the cylindrical type or the pillar type, in which a center of the pan part is recessed, or a structure in which a steric projection or concavity is disposed on a recessed bottom of the pan type part in order to increase specific surface area, depending on a culture purpose.

A culture medium 3 is contacted with a part of a microporous body 2, is transferred upwardly via communicating pores in the interior of the microporous body due to capillary action, is retained in the interior thereof, and is supplied to an organism tissue or organism cell 4, whereby, propagation, dedifferentiation, differentiation, regeneration, preservation, selection, isolation and cross of an organism tissue can be induced. Further, according to the embodiment of the present invention, at the start of culture a organism tissue or cell which is seeded on the microporous body without contacting with the culture medium sometimes grows big and comes in contact with the pooled culture medium in the process of culture. This case is also included within the scope of the present invention.

Figure 2:
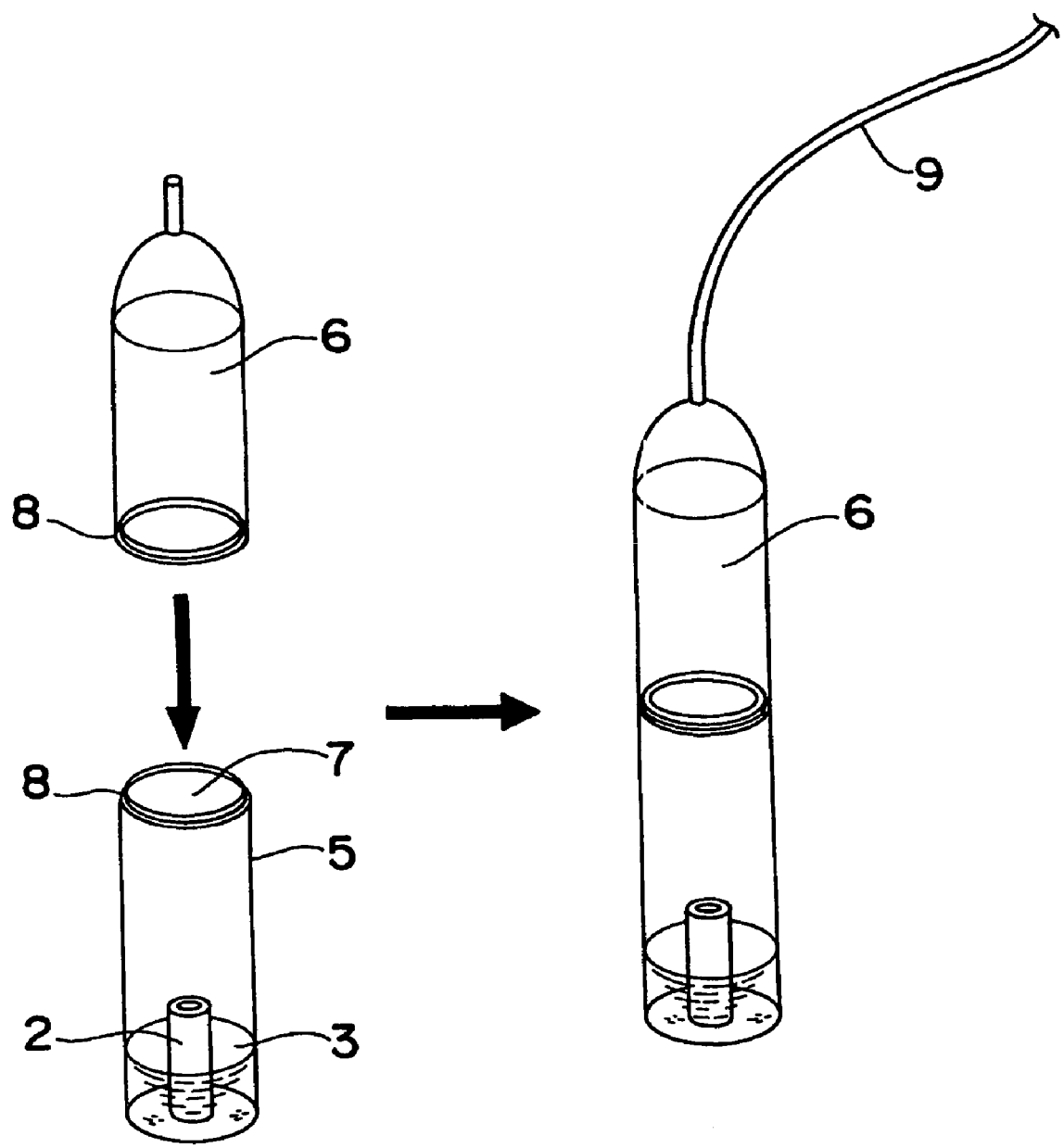
FIG. 2 is a perspective view from an upper visual point showing another embodiment of the culturing apparatus of the present invention.
Figure 3:
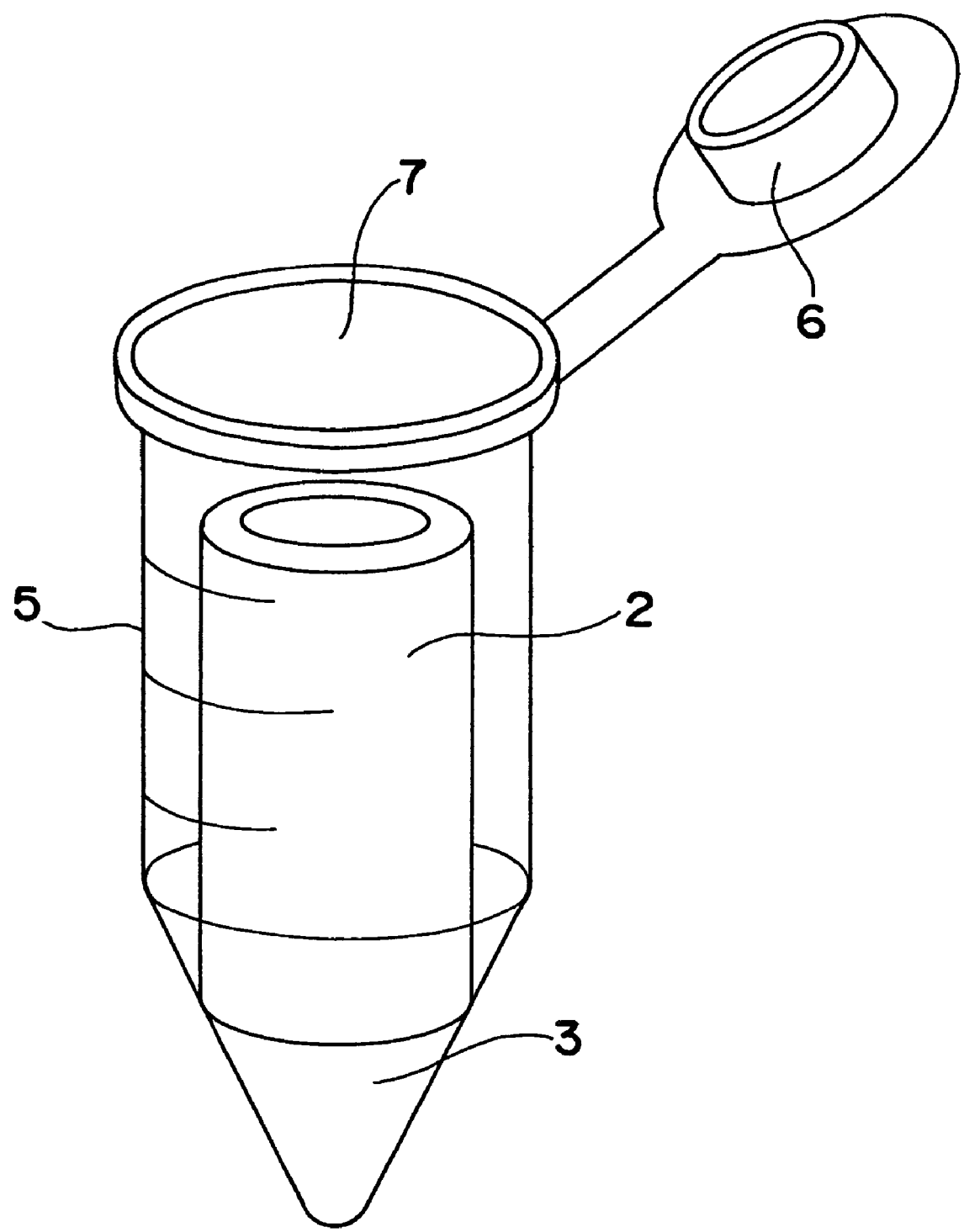
FIG. 3 is a perspective view from an upper visual point showing another embodiment of the culturing apparatus of the present invention.

A container 5 containing at least a part of the aforementioned culture medium 3 and microporous body 2 is enough as far as, by sealing an opening of the container with an aluminum foil, the microporous body 2, the culture medium 3 and the organism tissue or the organism cell 4 can be shut off from the outside of the container. Preferably, the container is resistant to high temperature and high pressure sterilizing treatment such as treatment with an autoclave, and various culturing conditions and culture medium conditions such as strong alkaline, strong acidic, high temperature, low temperature, high salt concentration, high pressure, low pressure, organic solvent, radiation or applying gravity condition or the like, has material and shape by which the culture status can be observed from the outside, is made of materials which are generally used as a tissue culture container such as glass, plastic and vinyl polymer, and has shapes such as cylinder type, flat-bottom flask type, cup type, lattice type and plate type. In addition, when an organism tissue or an organism cell is cultured by replacing the atmosphere in a container with a particular gas, and when an organism tissue or an organism cell is cultured by pressurizing or depressurizing the atmosphere in a container, a lid 6 and a container 7 are provided with a threading mechanism 8 which can engage so that the interior of a container can be kept sealed even under pressure or depressure conditions, and a feeding tube 9, as shown in FIG. 2 (when the atmosphere in the container is substituted by a particular gas, two or more feeding tubes are provided). Further, when an organism tissue or an organism cell is cultured by applying gravity, or when ingredients excreted from a cultured tissue a cultured cell are collected from the microporous body, centrifuging tube may be used as a container and a lid as shown in FIG. 3.

When an organism tissue is cultured using the organism-culture apparatus of the present invention, the following operations are usually performed.

First, a culture medium 3 and a microporous body 2 are placed into a container 5 through an opening 7, an opening 7 of the container is sealed with a plug 6 such as an aluminium foil, a cotton plug, a silicone plug, a rubber plug, and a cork plug, and it is confirmed that a culture medium 3 has been absorbed throughout a microporous body 2 and, thereafter, the organism-culture apparatus is subjected to high temperature and high pressure sterilizing treatment such as treatment with an autoclave. Alternatively, such the organism-culture apparatus may be subjected to non-heating sterilization such as ultraviolet sterilization.

Then, this organism-culture apparatus 1 is cooled to room temperature, a plug 6 is removed under the aseptic conditions such as in a clean bench, and then an organism tissue or an organism cell 4 which has been subjected to sterilization treatment in advance by the method well known by a person skilled in the art is placed on the surface of a microporous body 2 using an equipment such as a forceps, a pipette, a platinum loop and platinum needle. Thereafter, an opening 7 is sealed again with a plug, and an organism tissue or an organism cell 4 is cultured by standing, shaking, centrifuging or the like the culture apparatus 1 under the suitable condition.

Alternatively, the culture medium may be absorbed throughout a microporous body by subjecting a microporous body 2 placed in a container 5 and a culture medium 3 placed in another container to high temperature and high pressure sterilization dry heat sterilization separately, and dispensing a culture medium 3 in a container 5 under the aseptic conditions. Alternatively, a microporous body 2, and a culture medium 3 placed in a container are subjected to ultraviolet or gamma ray sterilization separately, and a microporous body 2 may be placed in a container containing a culture medium under the aseptic conditions.

In this embodiment, a microporous body 2 is disposed upright on a bottom of a container 5. However, in the organism-culture apparatus of the present invention, it is enough that a part of a microporous body 2 is disposed in a container 5 in such a positional relationship that the part is contacted with a culture medium 3 or is immersed in a culture medium 3. For example, a microporous body may be hung from a side or an upper part of a container 5 or a plug 6.

Figure 6:
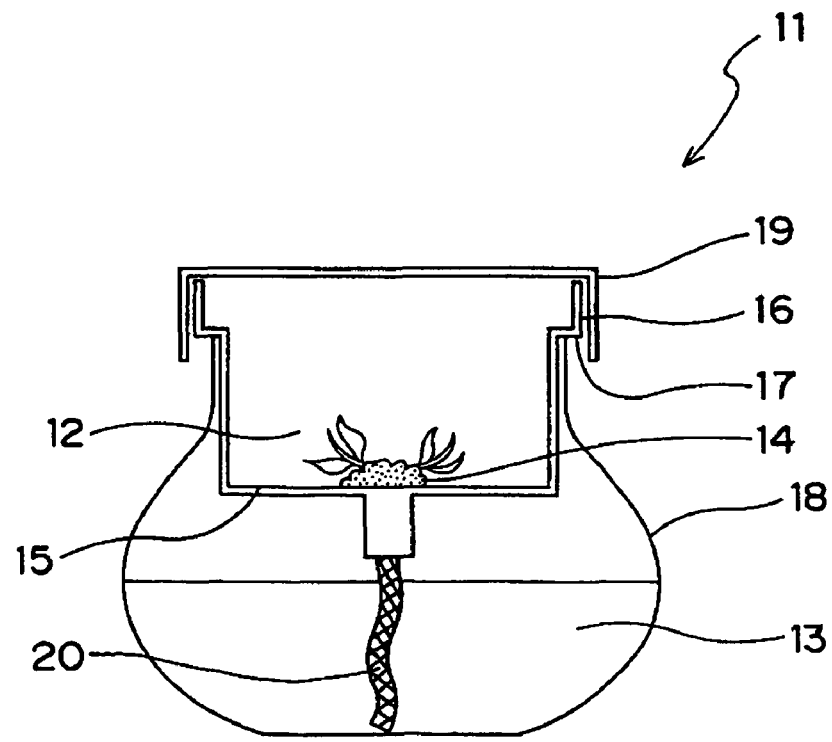
FIG. 6 is a cross-sectioned view from a side visual point showing another embodiment of the culturing apparatus of the present invention.
Figure 7:
FIG. 7 is a photograph as a substitute for a drawing showing a tobacco (*Nicotiana tabacum*) seed which has been germinated with a culturing apparatus 1 of the present invention which contains a culture medium containing a plant hormone.
Figure 8:
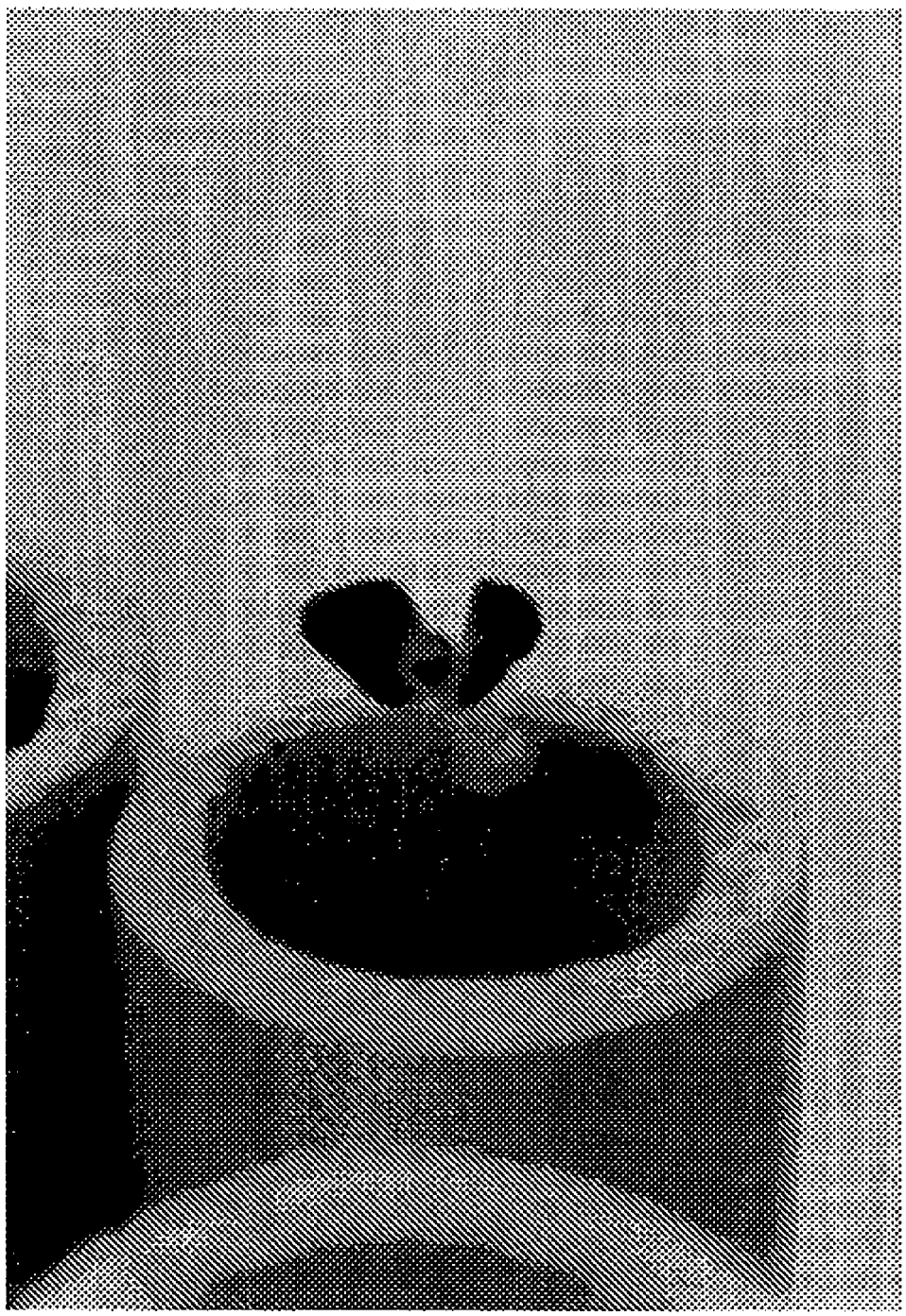
FIG. 8 is a photograph as a substitute for a drawing showing a tobacco (*Nicotiana tabacum*) callus at the day 10 after seeding which has been grown with a culturing apparatus 1 of the present invention which contains a culture medium containing a plant hormone.
Figure 9:
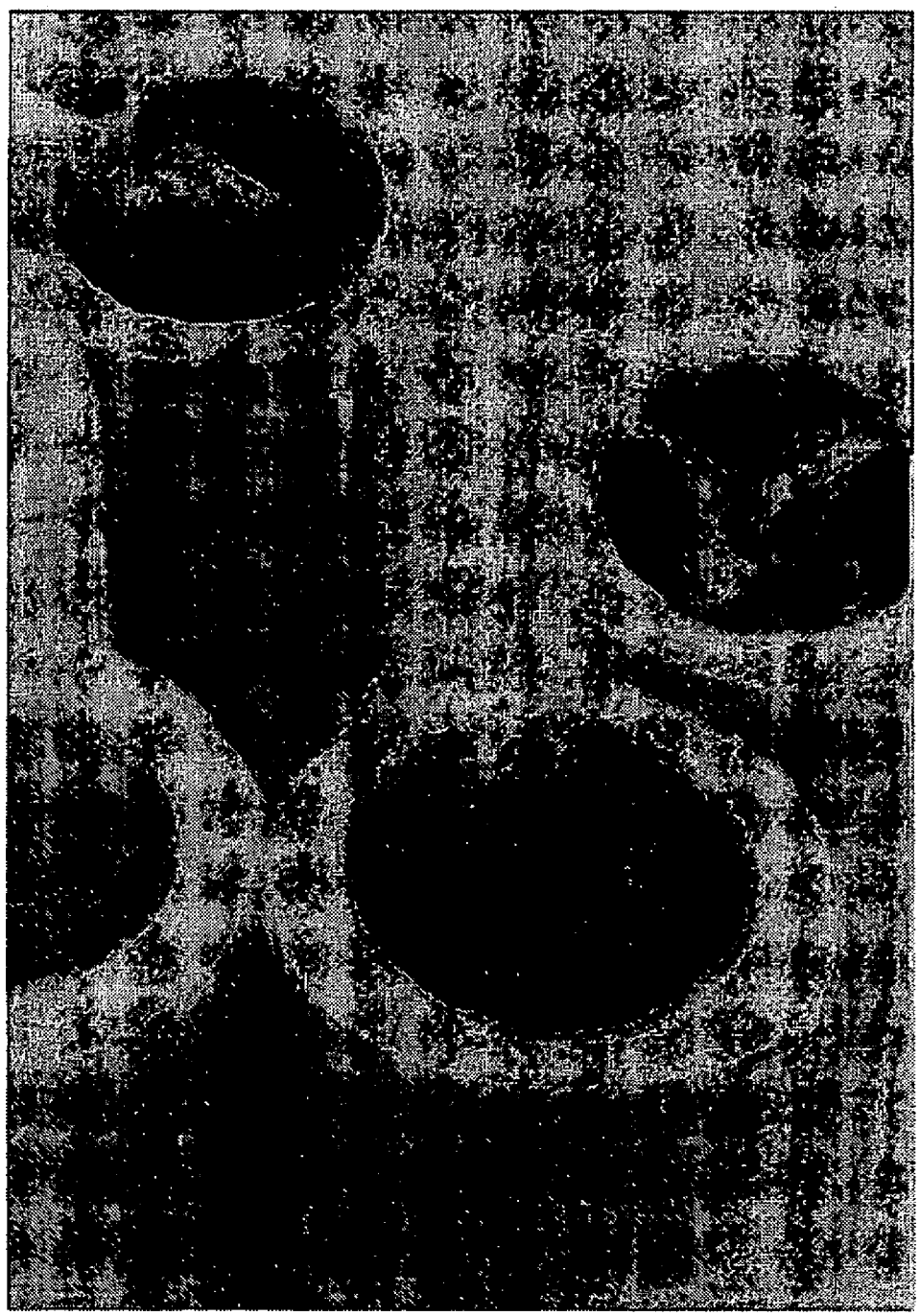
FIG. 9 is a photograph as asubstitute for a drawing showing a tobacco callus at the day 26 after seeding which has been grown with a culturing apparatus 1 of the present invention which contains a culture medium containing a plant hormone.
Figure 10:
FIG. 10 is a photograph as a substitute for a drawing showing a tobacco callus at the day 28 after seeding which has been grown with a culturing apparatus 1 of the present invention which contains a culture medium containing a plant hormone.
Figure 11:
FIG. 11 is a photograph as a substitute for a drawing showing a tobacco callus at the day 32 after seeding which has been grown with a culturing apparatus 1 of the present invention which contains a culture medium containing a plant hormone.

Alternatively, as shown in FIG. 6, an intervening body 20 composed of polyvinyl alcohol, carbon fiber bundle, glass fiber bundle or water-absorbing acryl fiber bundle is provided at a lower part of a microporous body 12 and, by immersing a part of the intervening body, a culture medium 3 can be penetrated into a microporous body via the intervening body. In addition, it is preferable that such the intervening body 20 has the flexibility. Then, by penetrating a culture medium into a microporous body via an intervening body by using the intervening body, it is possible to impart a degree of freedom to a size of a microporous body and that of a container. In addition, a precipitatable component contained in a culture medium can be prevented from being precipitated in pores of a microporous body by precipitating the precipitatable component on an intervening body by using the intervening body. In addition, it is preferable that the microporous body and the intervening body have the resistant to heat, low temperature, strong alkaline, strong acidic, organic solvent, radiation, ultraviolet ray, pressure, and depressure and have a strength such that a shape thereof is not deformed by a gravity.

The organism-culture apparatus of the present invention can be used for culture the plant tissue or cell such as of a seed, a leaf, a shoot apex, a stem, a root, an anther, a filament, a growing point (a terminal bud, a lateral bud, a shoot apex, a root apex), an axillary bud, a scale, an ovary, an ovule, an embryo, a pollen, an adventitious bud, an adventive embryo and an adventitious root of a useful tree such as bishop's flower (*Ammi majus*), onion (*Allium cepa*), garlic (*Allium sativum*), celery (*Apium graveolens*), asparagus (*Asparagus officinalis*), sugar beet (*Beta vulgaris*), cauliflower (*Brassica oleracea* var. *botrytis*), brusseles sprout (*Brassica oleracea* var. *gemmifera*), cabbage (*Brassica oleracea* var. *capitata*), rape (*Brassica napus*), caraway (*Carum carvi*), chrysanthemum (*Chrysanthemum morifolium*), spotted hemlock (*Conium maculatum*), coptis Rhizome (*Coptis japonica*), chicory (*Cichorium intybus*), summer squash (*Curcurbita pepo*), thorn apple (*Datura meteloides*), carrot (*Daucus carota*), carnation (*Dianthus caryophyllus*), buckwheat (*Fagopyrum esculentum*), fennel (*Foeniculum vulgare*), strawberry (*Fragaria chiloensis*), soybean (*Glycine max*), hyacinth (*Hyacinthus orientalis*), sweet potato (*Ipomoea batatas*), lettuce (*Lactuca sativa*), birds-foot trefoil (*Lotus corniculatus, Lotus japonicus*), tomato (*Lycopersicon esculentum*), alfalfa (*Medicago sativa*), tobacco (*Nicotiana tabacum*), rice (*Oryza safiva*), parsley (*Petroselinum hortense*), pea (*Pisum sativum*), rose (*Rosa hybrida*), egg plant (*Solanum melongena*), potato (*Solanum tuberosum*), wheat (*Triticum aestivum*), maize (*Zea mays*) and the like; a foliage plant such as snapdragon (*Antirrhinum majus*), mouse-ear cress (*Arabidopsis thaliana*), croton (*Codiaeum variegatum*), cyclamen (*Cyclamen persicum*), poinsettia (*Euphorbia pulcherrima*), barberton daisy (*Gerbera jamesonii*), sunflower (*Helianthus annuus*), fish geranium (*Pelargonium hortorum*), petunia (*Petunia hybrida*), African violet (*Saintpaulia ionatha*), dandelion (*Taraxacum officinale*), torenia (*Torenia fournieri*), Dutch clover (*Trifolium repens*), cymbidium (*Cymbidium*) and the like; a useful tree such as beat tree (*Azadirachta indica*), orange (*Citrus*), common coffee (*Coffea arabica*), ribbon gum (*Eucalyptus*), para rubber tree (*Hevea brasiliensis*), holly (*Ilex aquifolium*), trifoliate orange (*Poncirus trifoliata*), almond (*Prunus amygdalus*), carolina poplar (*Populus canadensis*), oriental arborvitae (*Biota orientalis*), Japanese ceder (*Cryptomeria japonica*), Norway spruce (*Picea abies*), pine genus (*Pinus*), grapevine (*Vitis vinifera*), apple (*Malus pumila*), apricot (*Prunus armeniaca*), persimmon (*Diospyros kaki*), fig (*Ficus carica*), chestnut (*Castanea crenata*) and the like; an animal cell such as a lung fibroblast, an epidermal cornified cell, a melanocyte, a dermal fibroblast, a bronchial epithelial cell, a bronchial smooth muscle cell, an epithelial cell of proximal urinary tubule, a cortex renis epithelial cell, a mesangial cell, a bronchiole epithelial cell, an astrocyte, an endothelial cell of umbilical cord blood vessel, an endothelial cell of coronary blood vessel, a smooth muscle cell of coronary blood vessel, a synovial cell, an endothelial cell of aorta, a smooth muscle cell of aorta, an endothelial cell of pulmonary artery, a smooth muscle cell of pulmonary artery, an endothelial cell of pulmonary micro-blood vessel, an endothelial cell of dermal micro-blood vessel, an iliac endothelial cell, an endothelial cell of micro-blood vessel of newborn infant, a human hair dermal papilla cell, a chondrocyte, a bovine coronary artery endothelial cell, a bovine coronary artery smooth muscle cell, a chicken aortic smooth muscle cell, a mouse cerebral microtubule endothelial cell, a porcine liver macrophage, a porcine testicle macrophage, a rat aortic smooth muscle cell, a rat preadipocyte and the like of an animal such as a human being (*Homo sapiens*), a Japanese macaque (*Macaca fuscata*), a rhesus macaque (*Macaca muulatta*), a chimpanzee (*Pan troglodytes*), an orang-utan (*Pongo pygmmaeus*), a pig (*Sun scrofa*), a mouse (*Mus musculus*), a rat (*Rattus norvegicus*), a domestic fowl (*Allus gallus*) and the like, a mycelium or cell of a fungus such as enoki mushroom (*Flammlina velutipes*), shiitake mushroom (*Lentinula edodes*), bunashimeji mushroom (*Hypsizygus marmoreus*), fried chicken mushroom (*Lyophyllum decastes*), nameko mushroom (*Pholiota nameko*), inky cap (*Coprinus atramentarius*), sulphur tuft (*Naematoloma sublateritium*), puffball (*Lycoperdon gemmatum*), mannentake muchroom (*Ganoderma lucidum*), suehirotake muchroom (*Schizophyllum commune*), oyster mushroom (*Pleurotus ostreatus*), maitake mushroom (*Grifola frondosa*), matsutake mushroom (*Tricholoma matsutake*), yanagimatsutake mushroom (*Agrocybe cylindracea*), turkey tails (*Coriolus versicolor*), brown yellow boletus (*Suillus luteus*), larch boletus (*Suillus grevillei*), amihanaiguchi (*Boletinus cavipes*), honshimeji mushroom (*Lyophyllum shimeji*), *Mucor, Rhizopus, Absidia, Phycomyces, Aspergillus* such as *Aspergillus niger, Aspergillus oryzae* and *Aspergillus tamarii* and the like, *Penicillium, Fusarium, Trichoderma, Monilia* as well as yeast (*Saccharomyces cer-* evisiae) and the like; a bacterim such as photosynthetic bacteria (Rhodospillum molischianum, Rhodopseudomonas acidophila, Rhodomicrobium vannielii, Chromatium vinosum, Thiocapsa roseopersicina, Thiopedia rosea, Chlorobium limicola, Chlorobium phaeovibrioides, Pelodictyon clathratiforme, purple photosynthetic bacteria (Ectothiorhodospira halophila)), gliding bacteria (Myxococcus fulvus, Myxococcus coralloides, Myxococcus stipitatus, Myxococcus xanthus), sheathed bacteria (Sphearotilus natans), budding bacteria, bacteria having having an appendage (Hyphomonas neptunium, Gallionella ferruginea), spirochetes (Spirochaeta icterohaemorrhagiae, Spirochaeta pallida, Spirochaeta aurantia), spirillum, spiral or twist bacteria, aerobic bacilli or cocci (Pseudomonas fluorescens, Pseudomonas aeruginosa, Pseudomonas ovalis, Pseudomonas gluconicum, Xanthomonas oryzae, Gluconobacter oxydans), nitrogen-fixing bacteria (Azotobacter chroococcum, Rhizobium leguminosarum, Rhizobium trifolii, Rhizobium meliloti, Rhizobium phaseoli, Rhizobium japonicum, Clostridium pasteurianum), Methylomonadaceae (Methylomonas methanica), acetic acid bacteria (Acetobacter aceti), a facultative anaerobic bacilli (Escherichia coil, Enterobacter aerogenes, typhoid bacilli (Salmonella typhi), Salmonella typhimurium, Salmonella enteritidis, dysentery bacilli (Shigella typhimurium), Serratia marcescescens, Proteus vulgaris, Vibrio cholerae, Vibrio parahaemolyticus), anaerobic bacteria (Bacteroides succinogenes), aerobic cocci or coccobacilli (Staphylococcus aureus, Staphylococcus epidermidis, Staphylococcus saprophyticus, Streptococcus pyogenes, Streptococcus agalactiae, Streptococcus viridans, Streptococcus pneumoniae, Enterococcus faecalis, Enterococcus faecium, Enterococcus avium, Corynebacterium diphtheriae, Bacillus subtilis, Bacillus anthracis, Bacillus cereus, anaerobic cocci (Nesseria gonorrhoeae), gram-negative lithotrophic bacteria (Nitrosomonas europaea, Nitrosococcus oceani, Nitrobacter hamburgensis, Nitrobacter vulgaris, Nitrobacter winogradskyi, Thiobacillus thiooxydans), gram-positive cocci (glutamic acid fermenting bacteria (Micrococcus glutamicus), Staphylococcus aureus, Spreptococcus lactis, Streptococcus bovis, Streptococcus mutans, Leuconostoc mesenteroides, Leuconostoc lactis, Pediococcus cerevisiae, Pediococcus acidilactici, Pediococcus pentosaceus, Lactobacillus delbrueckii, Lactobacillus rimae, Sporolactobacillus inulinus, Bacillus coagulans, Bacillus subtilis, Bacillus polymyxa, Bacillus maercerans, Bacillus pycnoticus, anthrax bacteria (Bacillus anthracis), butylic acid fermenting bacteria (Clostridium butyrium), acetone-butanol fermenting bacteria (Clostridium acetobutylicum), Clostridium sporogenes, Clostridium botulinum, Clostridium perfiingens, tetanus bacilli (Clostridium tetani), sulfuir reducing bacteria (Desulfotomaculum rumimis), spore sarcina (Sporosarcina ureae)), bacteria associated with mycobacteria (diphtheria (Corynebacterium diphtheriae), Corynebacterium fascians, Corynebacterium rathayi, Corynebacterium sepedonicum, Corynebacterium insidiosum, Corynebacterium flaccumfaciens, Actinomyces bovis, Nocardia farcinica, Streptomyces griseus, Streptomyces ramneus, Streptomyces venezuelae, Streptomyces omiyaensis, Streptomyces aureofaciens, Streptomyces avellaneus, Streptomyces lutianus), thermophilic bacteria (Aeropyrum pernix, Aquifex aeolicus, Archaeoglobus fulgidus, Bacillus thermoleovorans, Methanococcus jannaschii, Methanothermus fervidus, Pyrobaculum aerophilum, Pyrobaculum calidifontis, Pyrobaculum islandicum, Pyrobaculum oguniense, Pyrococcus furiosus, Pyrococcus horikoshii, Pyrococcus kodakaraensis, Pyrococcus shinkaj, Pyrolobus fumarii, Rhodothermus obamensis, Saccharopolyspora rectivirgula, Sulfolobus acidocaldarius, Sulfolobus shibatae, Sulfolobus shibatae, Sulfolobus solfataricus, Sulfolobus tokodaii, Thermoactinomyces vulgaris, Thermococcus celer, Thermococcus odakaraensis, Thermococcus litoralis, Thermococcus profindus, Thermococcus strain, Thermoplasma acidophilum, Thermoplasma volcanium, Thermotoga maritima, Thermotoga neapolitana, Thermus thermophilus), methane bacteria (Methanobacterium formicicum, Methanobacterium thermoautotrophicum, Methanobrevibacter arboriphilus, Methanobrevibacter ruminantium, Methanobrevibacter smithii, Methanococcus jannaschii, Methanoculleus chikugoensis, Methanopyrus kandleri, Methanosaeta concilii, Methanosarcina barkeri, Methanosarcina mazeii, Methanosphaera stadmaniae, Methanothermobacter thermautotrophicus), halophilic bacteria (Haloarcula japonica, Haloarcula marismortui, Halobacterium halobium, Halobacterium salinarium, Haloferax mediterranei, Haloferax volcanii, Halomonas variabilis, Natronobacterium pharaonis, Tetragenococcus halohila, Vibrio parahaemolyticus, Vibrio vulnificus), cryophilic bacteria (Colwellia psychrerythraea, Moritella marina, Yersinia enterocolitica, Yersinia pseudotuberculosis, Shewanella benthica), barophilic bacteria (Moritella japonica, Moritella yayanosii, Photobacterium profindum, Shewanella benthica, Shewanella violacea, Shewanella oneidensis), acidophilic bacteria (Aeropyrum pernix, Sulfolobus solfataricus, Sulfolobus tokodaii, Sulfolobus acidocaldarius, Thermoplasma acidophilum), alkaliphilic bacteria (Bacillus alcalophilus, Bacillus halodurans, Bacillus pasturii, Exiguobacterium aurantiacum), radiation-resistant bacteria (Deinococcus radiodurans, Micrococcus radiodurans, Bacillus cereus), petroleum catabolizing bacteria HD-1 strain which was isolated at an oil field in Shizuoka Prefecture ($CO_2$-fixing type petroleum synthesizing or degrading bacteria), TK-122 strain, and organic solvent-resistant bacteria (Pseudomonas putida IH-2000 strain) and the like. As a specific culture method, any culturings known in the art are possible. When a plant is a subject, examples thereof include dedifferentiation (callusing) and redifferentiation of a plant tissue, anther culture, shoot apex culture, protoplast culture, batch culture, clonal cell culture, seed culture, high density culture, cocultivation, nurse culture methods, a conditioning culture method, an isotope competition method, a direct labeling method, an ovary culture method, an ovule culture method, an embryo culture method, a pollen culture method, a synchronized culture method and the like. In addition, when fingi are a subject, examples thereof include isolation culture from parts such as stalk, upper part of stalk, gill and pileus of mushroom fruit-body, spore isolation culture, isolation culture from soil and air, subculturing from isolated fungus strain and the like. In addition, when animals are a subject, examples thereof include gastrointestinal epithelial cells culture, hepatocyte culture, human epidermal keratinocytes culture, vascular endothelial cells culture, renal cells culture, langerhans islet cells culture, fibroblast culture, muscle cells culture, myelocyte culture, cancer cells culture, neural cells culture, bronchial epithelium cells culture, neural cells differentiation culture, blood cells differentiation culture, embryonic stem cells differentiation culture and hepatocarcinoma cells differentiation culture. Further, when bacteria are a subject, examples thereof include anaerobic culture using nitrogen, carbon dioxide or the like as the atmosphere, aerobic culture using air, pressurized oxygen or the like, culturing under strong alkaline condition, culture under strong acidic condition, culture at high temperature, culture at low temperature, culture at a high salt concentration, pressurized culture which is performed in the atmosphere exceeding the atmospheric pressure, depressurized culture, culture in an organic solvent, culture under radiation, and culture which is performed with applying gravity by centrifuging.

Figure 4:
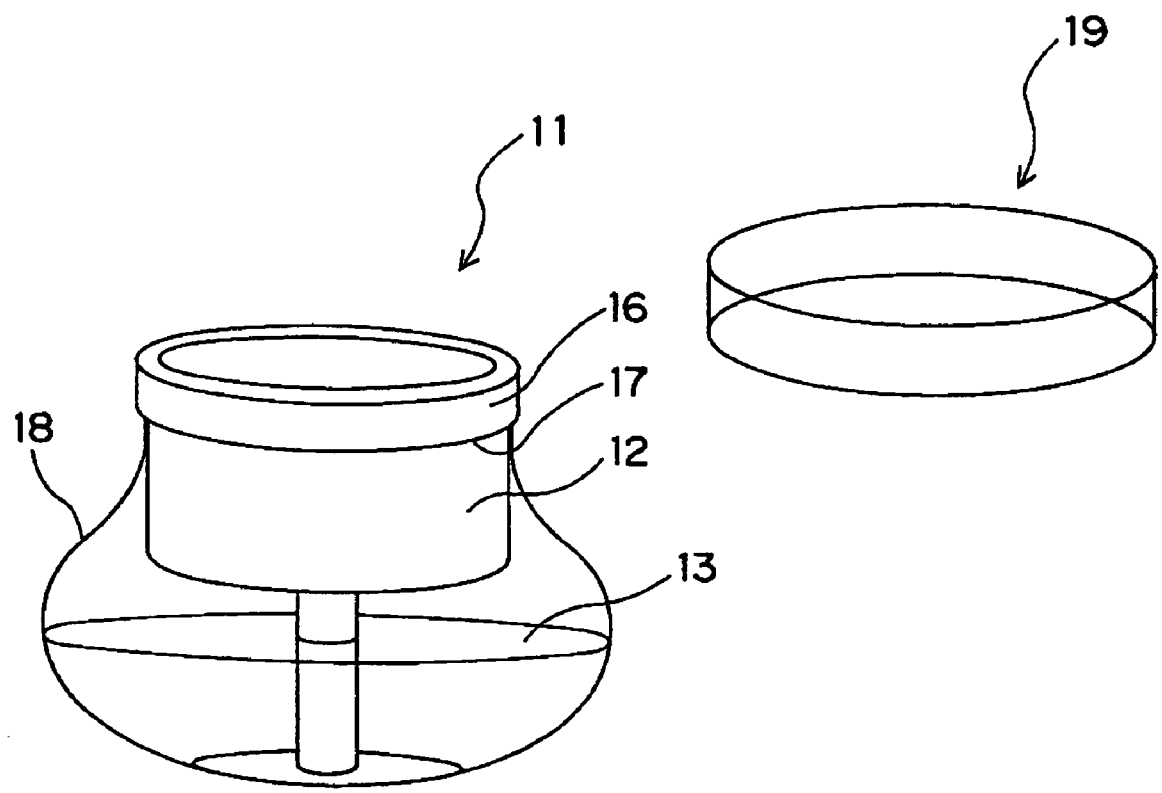
FIG. 4 is a perspective view from an upper visual point showing another embodiment of the culturing apparatus of the present invention.
Figure 5:
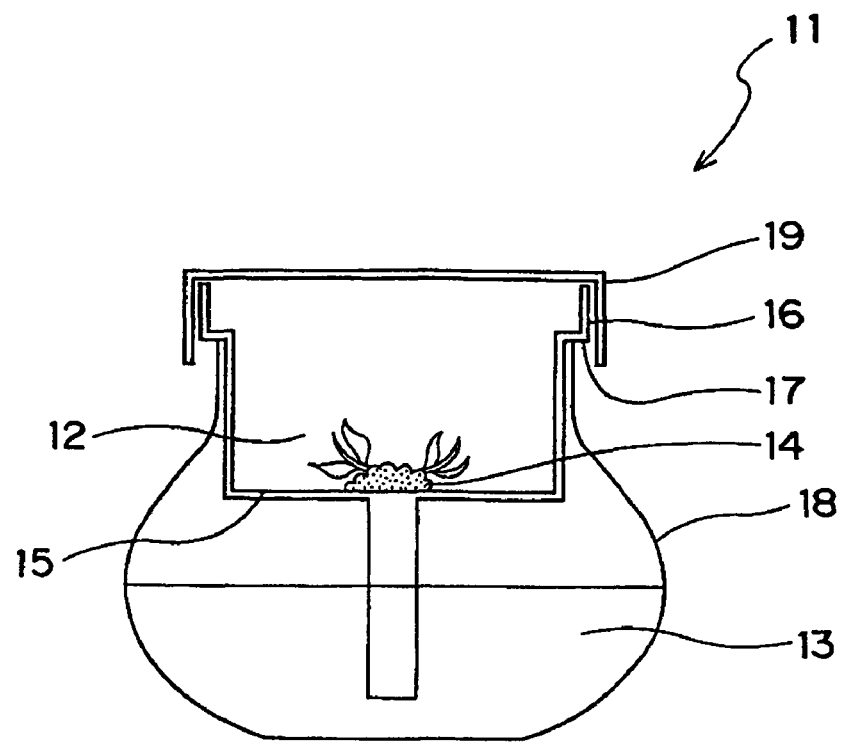
FIG. 5 is a cross sectioned view from a side visual point showing another embodiment of the culturing apparatus of the present invention.

The second embodiment of the organism-culture apparatus of the present invention is an organism-culture apparatus 11 comprising a culture medium 13, and a microporous body 12 comprising a cylindrical part and a pan type part continuing upwardly from the cylindrical part and having a larger outer diameter than that of the cylindrical part, and which can induce propagation, dedifferentiation, differentiation, regeneration, preservation, selection, isolation and cross by placing an organism tissue 14 on a bottom 15 of a pan part in which a center thereof is recessed, as shown in FIG. 4 and FIG. 5. A microporous body 12 comprising a cylindrical type part and a pan type part is supported by a container 18 and seals the interior of the container by contact between a bottom 17 of a part 16 which projects in a diametric direction of the pan type part and a periphery of an opening of a container. Alternatively, a pan type part 12 of a microporous body can be sealed by fitting thereto a lid 19 which has material and shape by which the culturing status can be observed from the outside, such as a petri dish having an inner diameter corresponding to or greater than an outer diameter of the pan type part. Alternatively, a pan type part may be simply sealed with an aluminum foil as explained in the first embodiment. In addition, a lid 19, a container 18 on a part 16 joint parts and feeding tube. This apparatus can keep sealed even under pressure or depressure. In addition, it is preferable that the microporous body has the resistant to heat, strong alkaline, strong acidic, high pressure, low pressure, organic solvent, radiation, ultraviolet or the like.

Since a culture medium, a raw material and a material of a microporous body, and an organism tissue or an organism cell which can be a culturing subject are the same as those of the first embodiment, explanation thereof is omitted.

MODE FOR CARRYING OUT THE INVENTION

Examples

In order to make clear that organism cells can be cultured using the organism-culture apparatus of the present invention, the following apparatuses and samples were used to perform experiments.

Culture Experiment 1

(1) Culture Apparatus

A cylindrical type microporous body having an outer diameter of 1.4 cm, an inner diameter of 0.9 cm and a height of 4.5 cm which had been prepared by firing at 1250° C. for 24 hours while containing 50-60% by weight of alumina $Al_2O_3$ in Murakami clay (manufactured in Niigata Prefecture in Japan), was disposed upright on a bottom of a glass flat-bottom test tube having a diameter of 2.3 cm and a height of 15 cm, and 6 ml of a dedifferentiation MS liquid culture medium containing each 2 ppm of naphthalene acetic acid (NAA) and benzyladenine (BA) was poured therein. Thereafter, an opening of the glass flat-bottom test tube was sealed with a doubled aluminium foil. After it was confirmed that a culture medium was absorbed throughout the microporous body in the test tube, this was sterilized at a high temperature and a high pressure for 10 minutes using an autoclave (121° C., pressurized at 1.2 atm), and allowed to cool to obtain a culture apparatus 1. The microporous body used in the experiment had the heat resistance.

Separately, a microporous body composed of a pan type part having an outer diameter of 7.5 cm, an inner diameter of 5.5 cm and a depth of 5.0 cm and a cylindrical part having an outer diameter 1.7 cm, an inner diameter of 0.7 cm and a height of 4.7 cm, and having a pillar type part having an outer diameter of 1.5 cm and a height 4.3 cm and projecting upwardly on a bottom of the part in which a center of the pan type part is recessed, which had been prepared using the same raw materials and conditions as those for the above culture apparatus 1, was fitted in a glass container having a volume of 570 ml, and an opening of the pan type part was sealed by covering with a petri dish. That was dry-heated to sterilize for 2 hours in a heater (161° C.). On the other hand, a dedifferentiation MS liquid culture medium containing each 2 ppm of naphthalene acetic acid (NAA) and benzyladenine (BA) was poured into an Erlenmeyer flask, and sterilized at a high temperature and a high pressure for 10 minutes using an autoclave (121° C., pressurized at 1.2 atm). Then, under the aseptic conditions, the microporous body was lifted slightly to detach from the container, and 130 ml of a dedifferentiation MS liquid culture medium which had been sterilized was poured therein through a gap. Thereafter, this was allowed to stand until the culture medium was absorbed throughout the microporous body, to obtain a culture apparatus 2.

(2) Test Material

As a test material, a seed and a leaf of an immature tobacco SR1 (*Nicotiana tabacum*) of 17 days after germination, and anther in a bud of strawberry (*Fragaria chiloensis*) having a diameter of 3 mm were used. These test materials were sterilication-treated by washing with flowing water, immersing in 70% ethanol for a few seconds, immersing in a 5% aqueous sodium hypochlorite solution for 10 minutes to used. As an anther in a strawberry bud, an anther was separated under the aseptic conditions from the bud which had been sterilization-treated as described above, and was used as a test material.

(3) Culture

The aluminium foil was removed from the culture apparatus 1 under the aseptic conditions, the test material was placed on an inner surface at a top of the microporous body and an opening was sealed with the aluminum foil again. Separately, the petri dish was removed from the culture apparatus 2 under the same conditions, the test material was placed on a bottom of the pan type part of the microporous body, and an opening of the pan type part was sealed with the petri dish again. Like this, the test material placed on the culture apparatus 1 or 2 was subjected to stationary culture at 26° C. under the natural sunshine conditions (around 10 cm beyond a frosted glass).

(4) Results (i) Tobacco Seed

Figure 12:
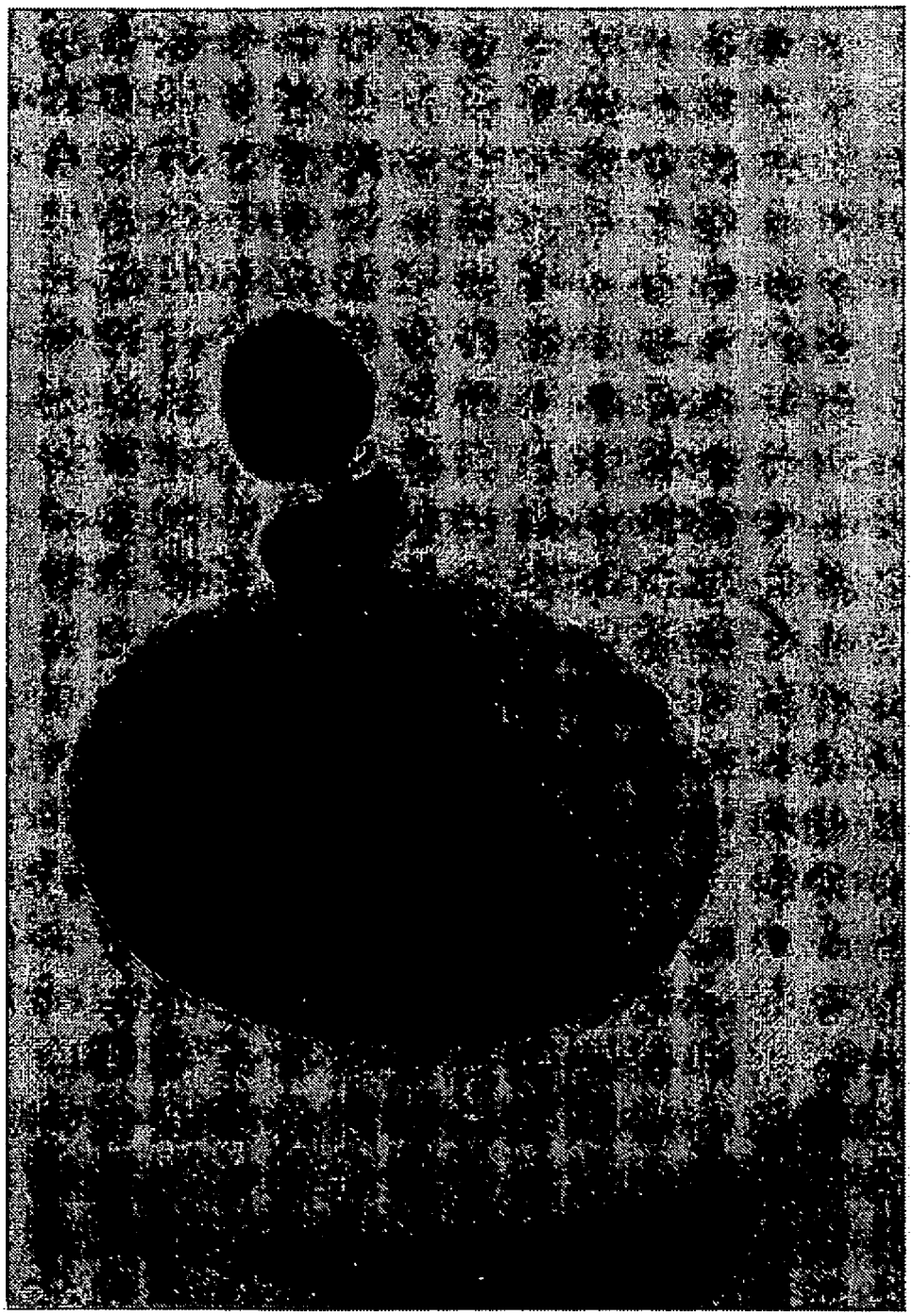
FIG. 12 is a photograph as a substitute for a drawing showing a tobacco seed which has been germinated with a culturing apparatus 1 of the present invention which contains a culture medium containing a plant hormone.
Figure 13:
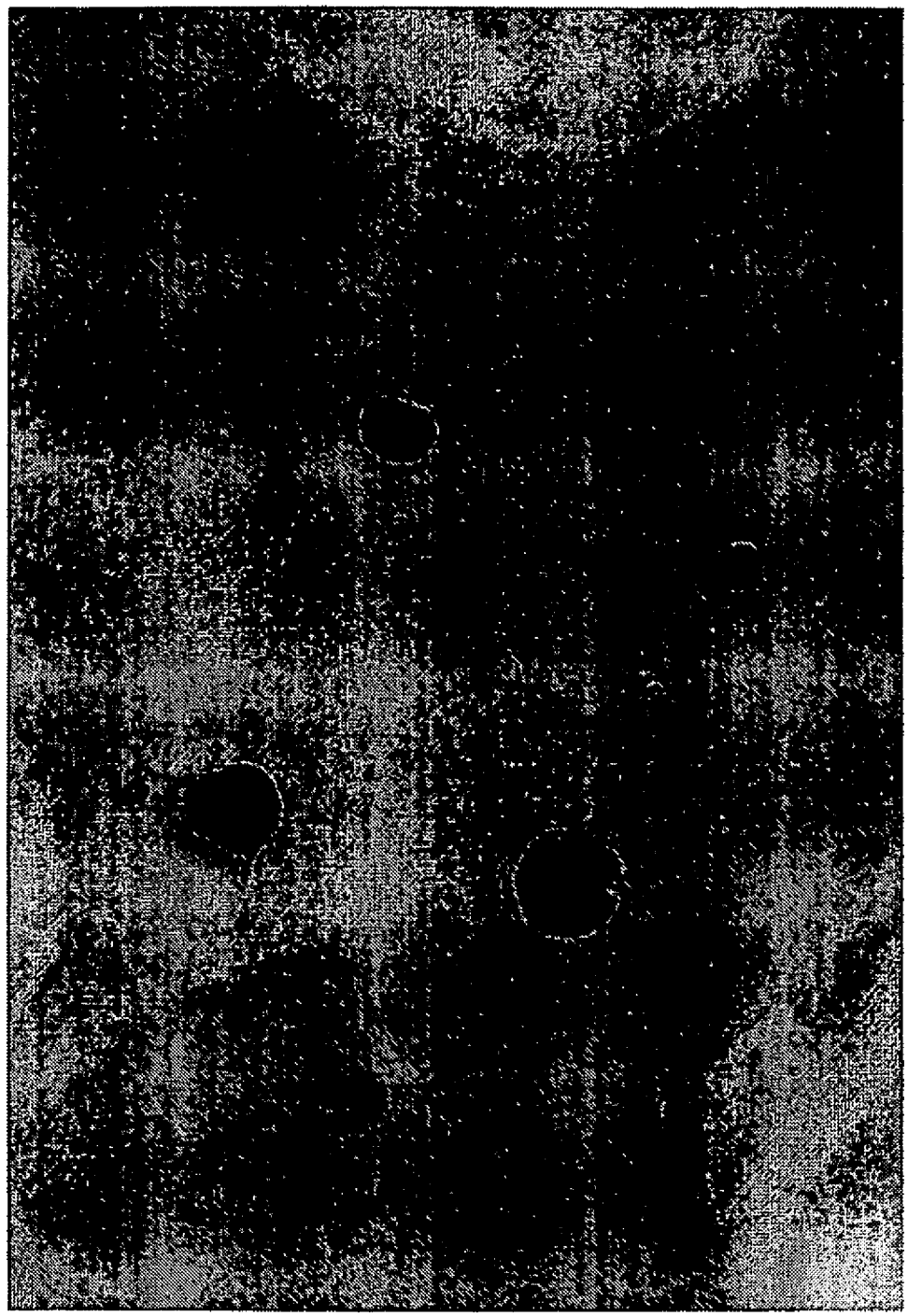
FIG. 13 is a photograph as a substitute for a drawing showing a leaf and a top of a tobacco seedling immediately after it is placing it on the culturing apparatus 2 of the present invention which contains a culture medium containing a plant hormone.
Figure 14:
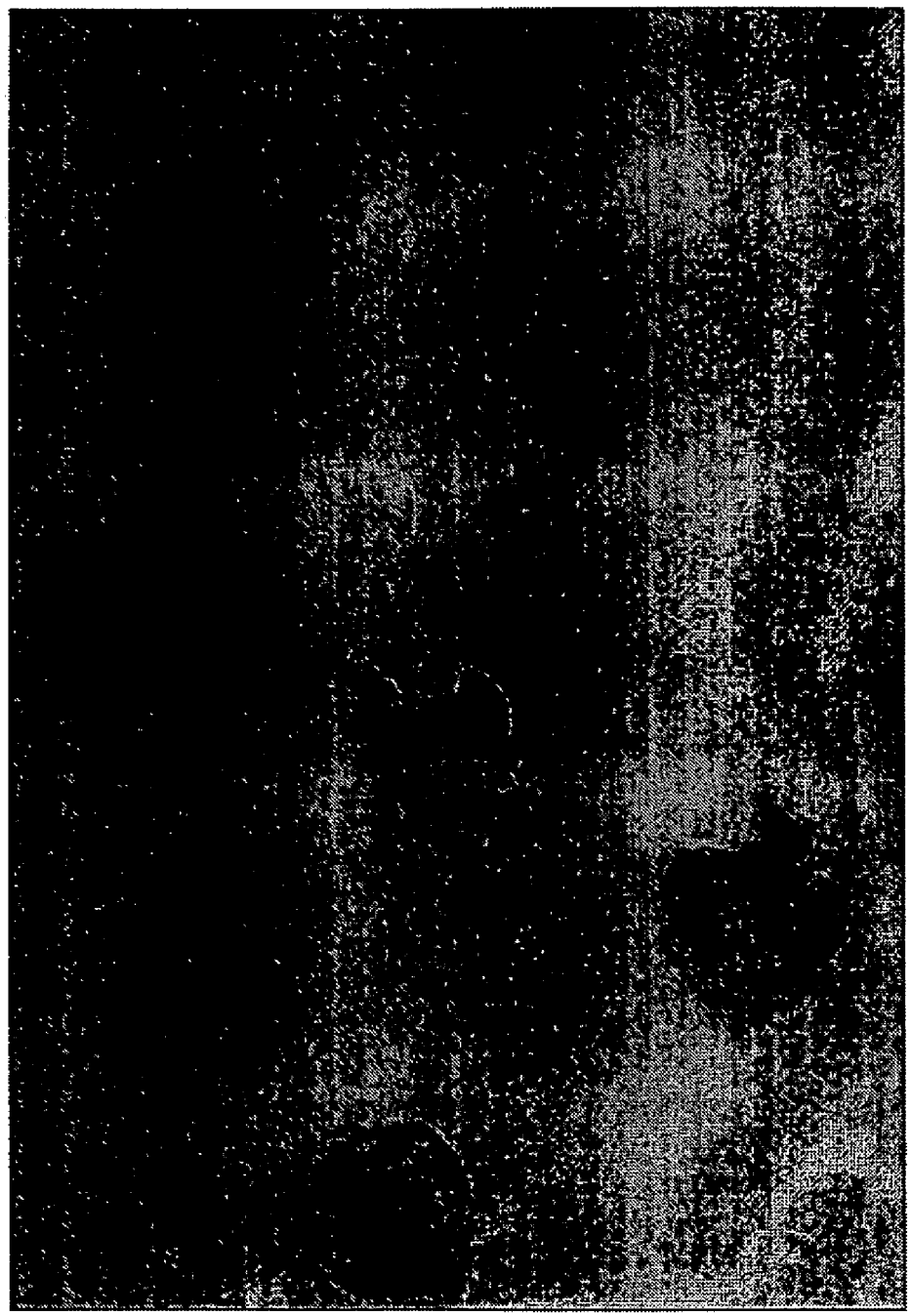
FIG. 14 is a photograph as a substitute for a drawing showing a tobacco callus at the day 10 after placed on the culturing apparatus 2 of the present invention which contains a culture medium containing a plant hormone.
Figure 15:
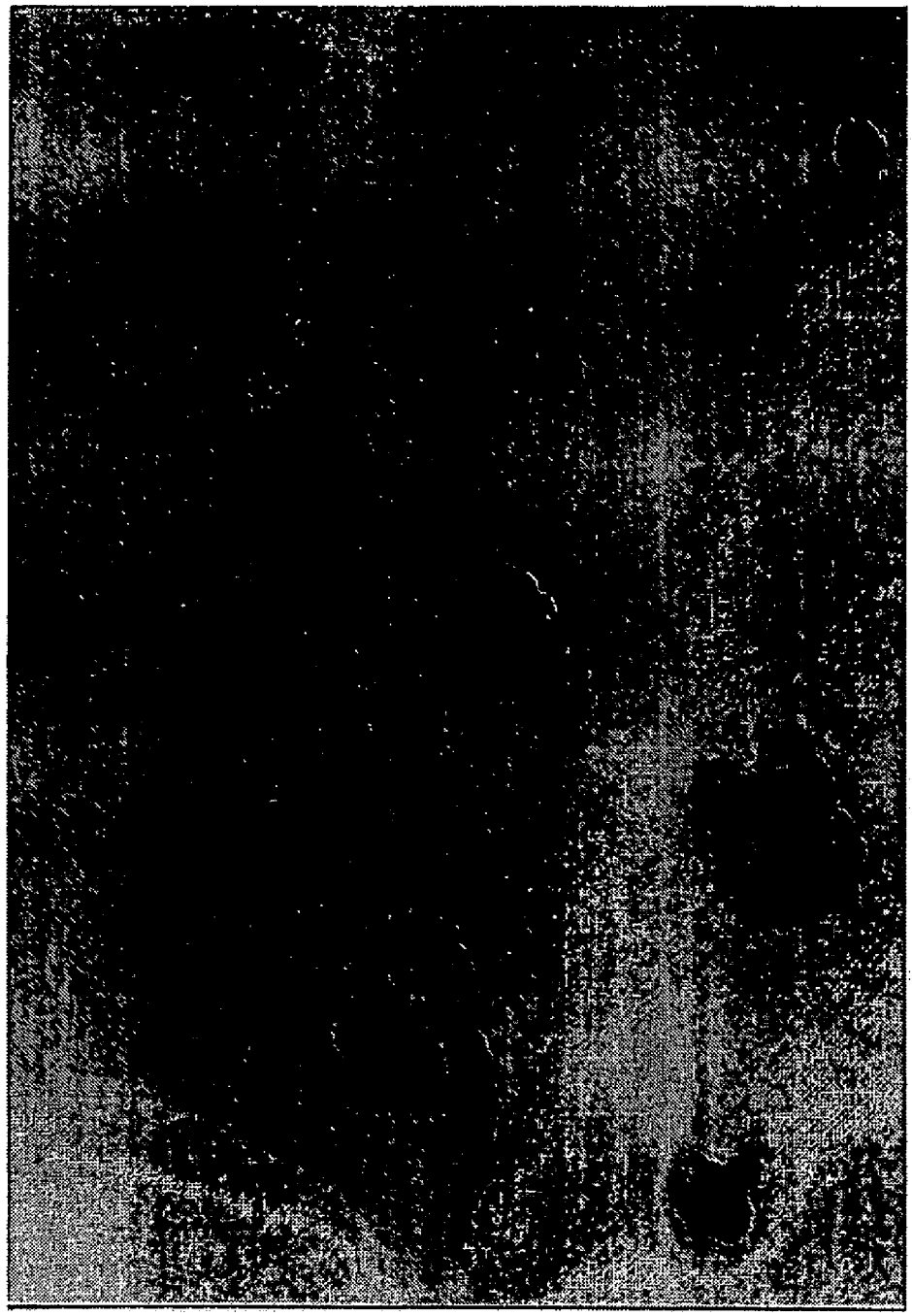
FIG. 15 is a photograph as a substitute for a drawing showing a tobacco callus at the day 33 after placed on the culturing apparatus 2 of the present invention which contains a culture medium containing a plant hormone.
Figure 16:
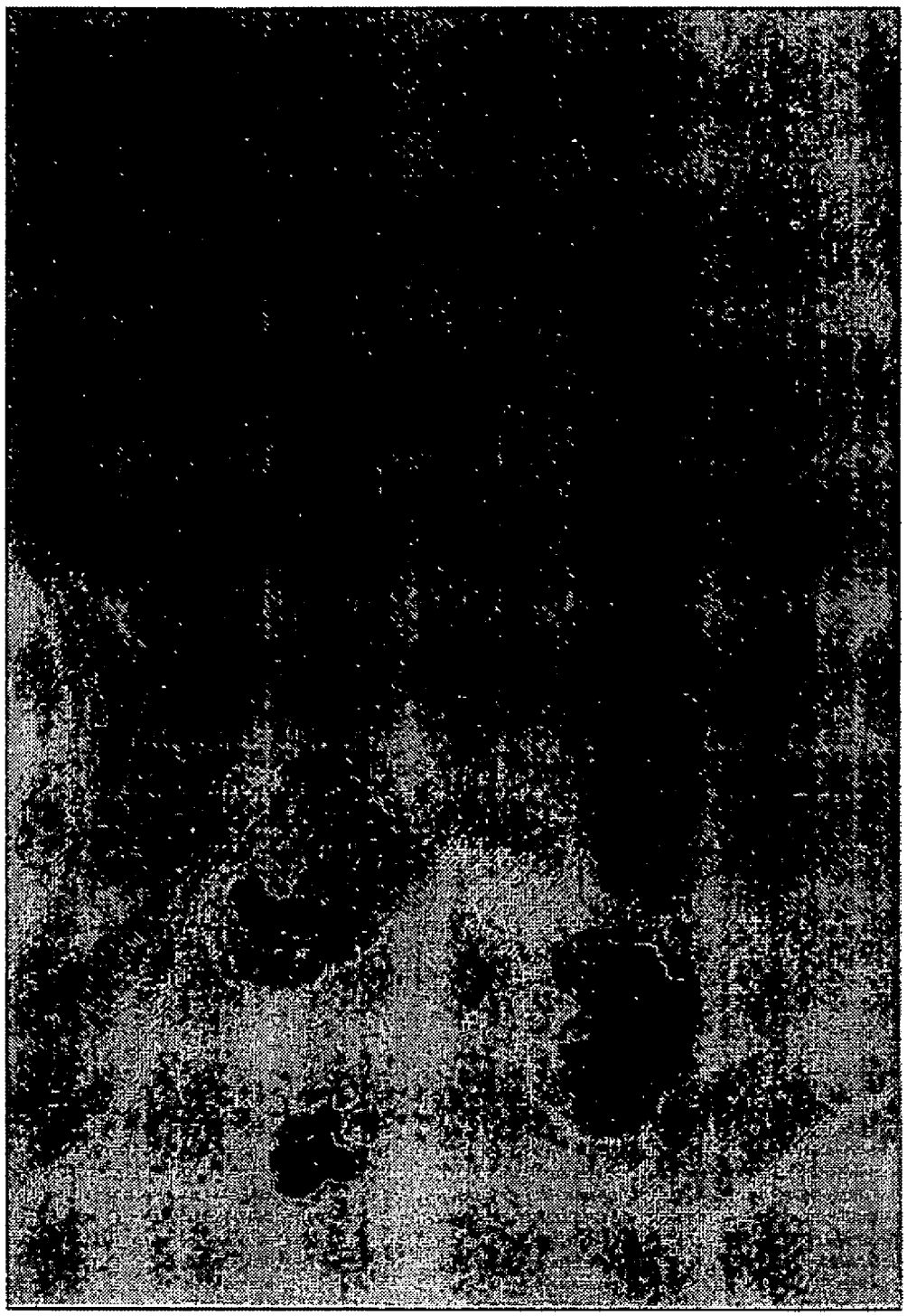
FIG. 16 is a photograph as a substitute for a drawing showing a tobacco callus at the day 56 after placed on the culturing apparatus 2 of the present invention which contains a culture medium containing a plant hormone.

Process of growth of a tobacco seed placed on the culture apparatus 1 as described above is shown in Table 1 and the statuses at the days 5, 10, 26, 28 and 32 after placement are shown in FIGS. 7-11, respectively. Separately, growth of a tobacco seed which was cultured with a culture medium containing neither NAA nor BA as a control is shown in FIG. 12.

TABLE 1

| Days after seeding | Process of growth of tobacco seed |
|---|---|
| Day 0 | Seeding |
| Day 5 | Germination, root being undifferentiated |
| Day 7 | Callused |
| Day 10 | Callus, diameter 0.8 mm |
| Day 26 | Callus, diameter 4.3 mm |
| Day 28 | Callus, diameter 5.0 mm |
| Day 32 | Callus, diameter 6.6 mm |

(ii) Leaf of Immature Tobacco

Process of growth of a leaf of immature tobacco plant which had been placed on the culture apparatus 2 as described above is shown in Table 2, and the statuses immediately after placement, the days 10, 33 and 56 after placement are shown in FIGS. 13 to 16, respectively.

TABLE 2

| Days after placement | Change in tobacco leaf and callus diameter |
|---|---|
| Day 0 | Placement, 3.1 mm |
| Day 10 | Callus, diameter 4 7 mm |
| Day 33 | Callus, diameter 4.9 mm |
| Day 56 | Callus, diameter 5.1 mm |

(iii) Anther of Strawberry

Figure 17:
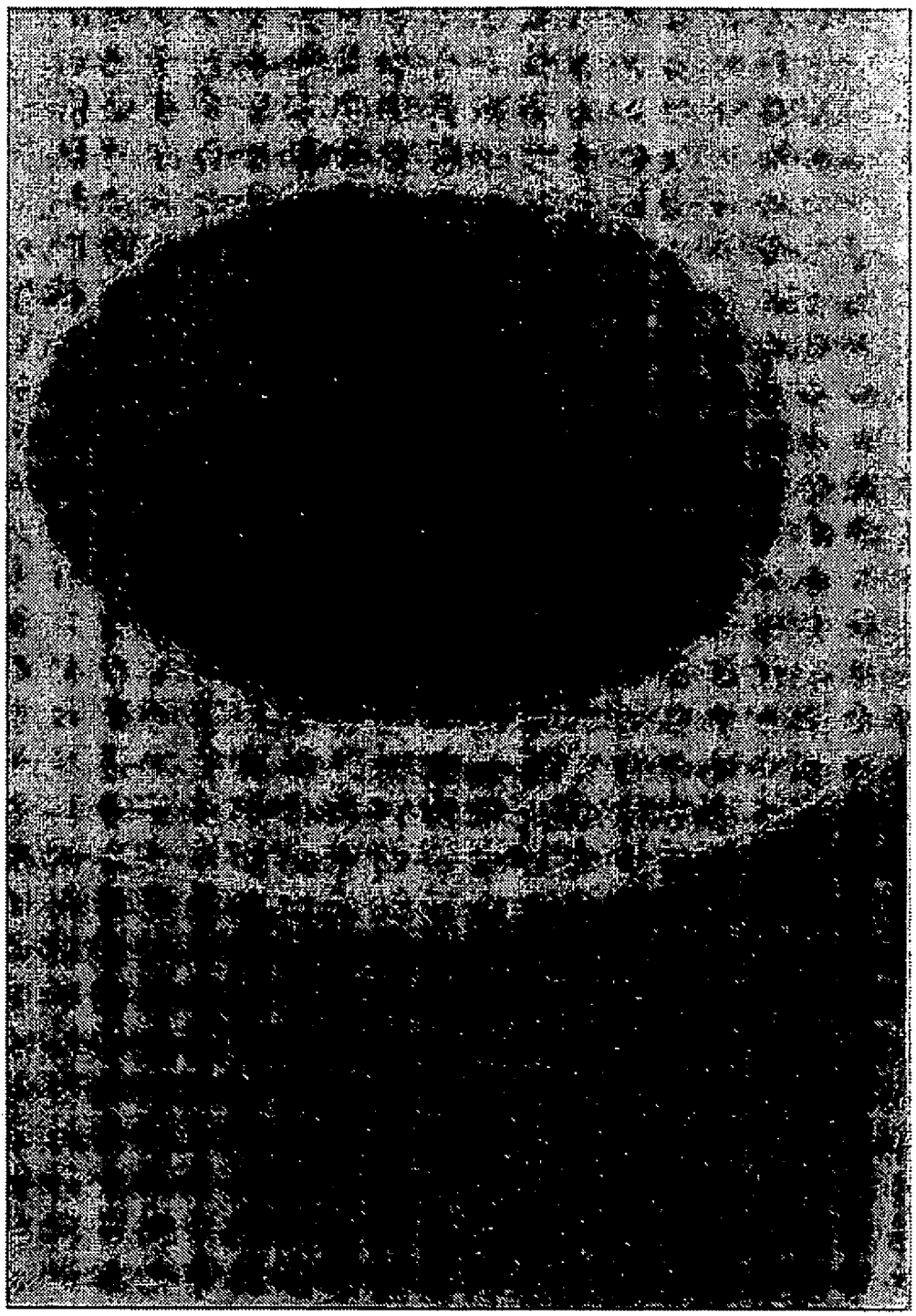
FIG. 17 is a photograph as a substitute for a drawing showing a strawberry (*Fragaria chiloensis*) anther on the day 35 after placed on the culture apparatus 1 of the present invention which contains a culture medium containing a plant hormone.
Figure 18:
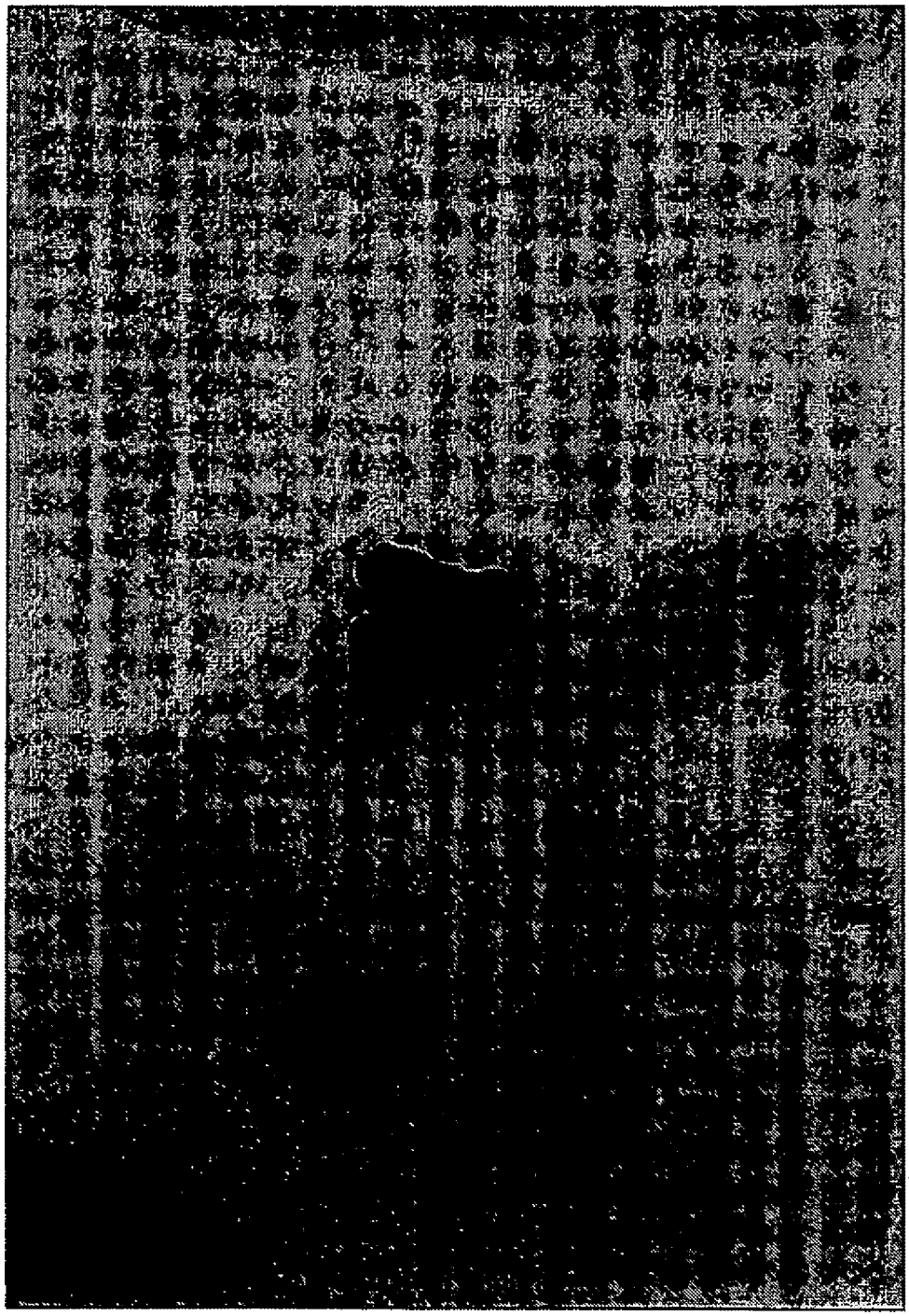
FIG. 18 is a photograph as a substitute for a drawing showing a fungus flora of filamentous fungus *Oospora roseoflava* 26 hours after seeded on the culture apparatus 2 of the present invention.
Figure 19:
FIG. 19 is a photograph as a substitute for a drawing showing a fungus flora of filamentous fungus *Oospora roseoflava* 49 hours after seeded on the culture apparatus 2 of the present invention.
Figure 20:
FIG. 20 is a photograph as a substitute for a drawing showing a fungus flora of filamentous fungus *Oospora roseoflava* 73 hours after seeded on the culture apparatus 2 of the present invention.
Figure 21:
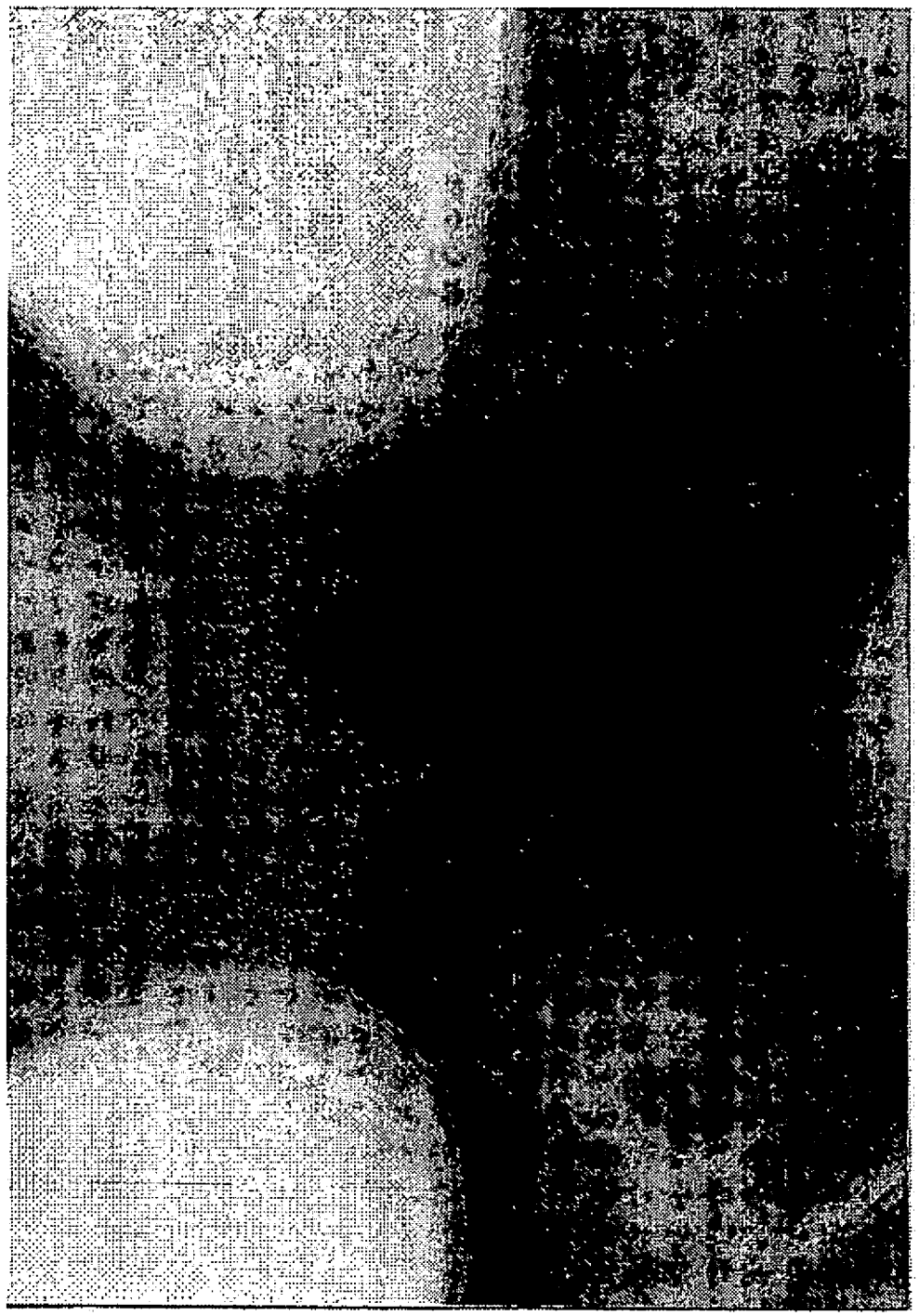
FIG. 21 is a photograph as a substitute for a drawing showing a fungus flora of filamentous fungus *Oospora roseoflava* 91 hours after seeded on the culture apparatus 2 of the present invention.
Figure 22:
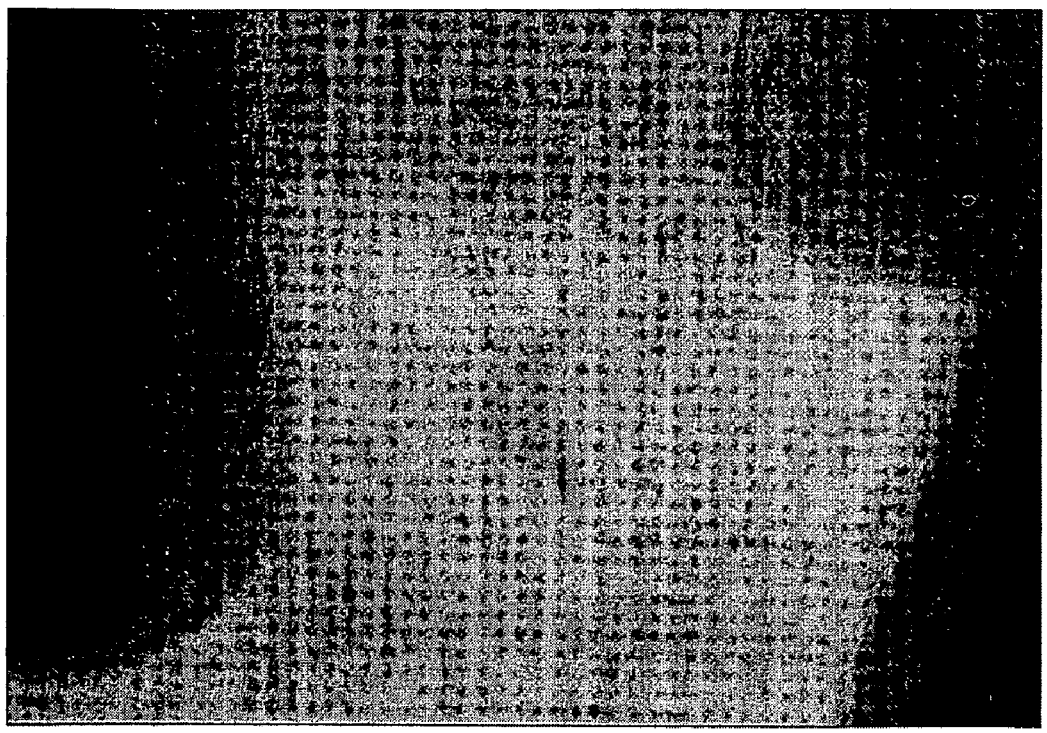
FIG. 22 is a photograph as a substitute for a drawing showing a fungus flora of enoki mushroom (*Flammulina velutipes*) on the day 10 after seeded on the culture apparatus 2 of the present invention.
Figure 23:
FIG. 23 is a photograph as a substitute for a drawing showing a fungus flora of enoki mushroom on the day 11 after seeded on the culture apparatus 2 of the present invention.
Figure 24:
FIG. 24 is a photograph as a substitute for a drawing showing a fungus flora of enoki mushroom on the day 13 after seeded on the culture apparatus 2 of the present invention.
Figure 25:
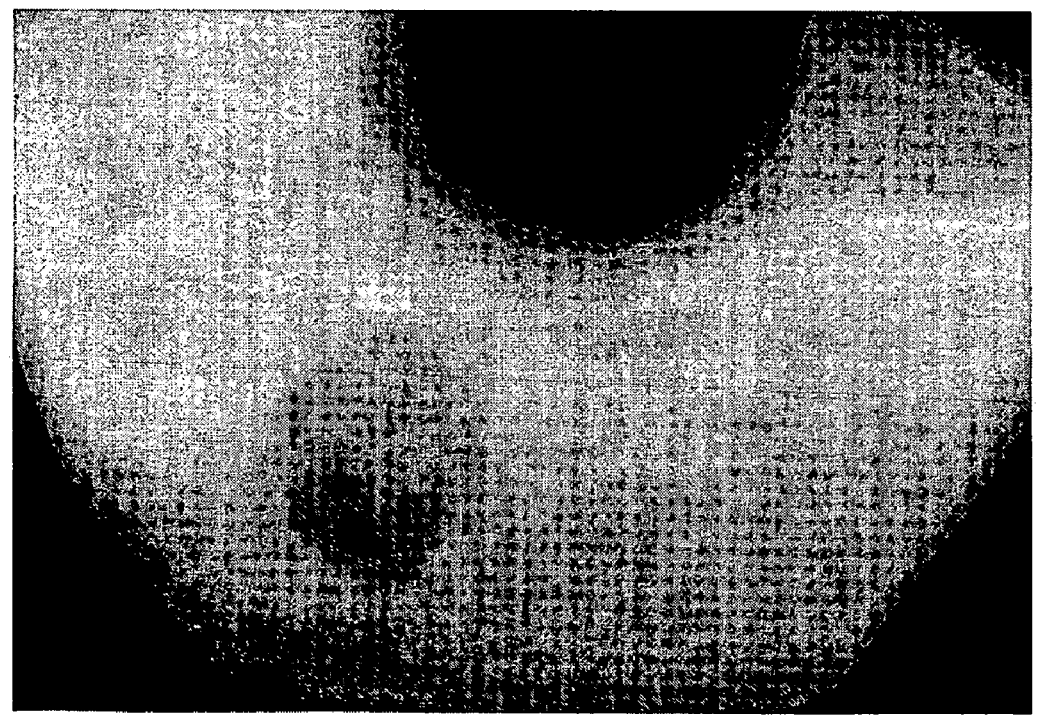
FIG. 25 is a photograph as a substitute for a drawing showing a fungus flora of enoki mushroom on the day 14 after seeded on the culture apparatus 2 of the present invention.
Figure 26:
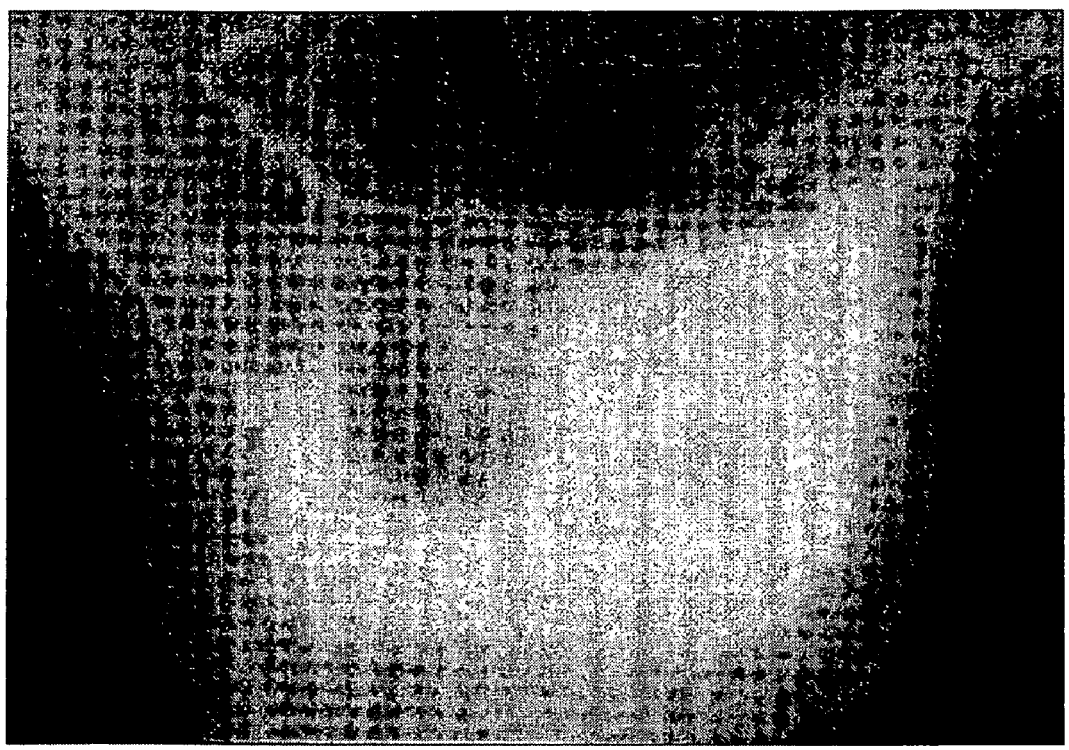
FIG. 26 is a photograph as a substitute for a drawing showing a fungus flora of enoki mushroom on the day 16 after seeded on the culture apparatus 2 of the present invention.

Process of growth of an anther of strawberry placed on the culture apparatus 1 as described above (N=29) is shown in Table 3. In addition, a photograph of a callus of a strawberry anther on the day 35 after placement is shown in FIG. 17.

TABLE 3

| Sample No. 26 Days after seeding | Process of growth of strawberry anther |
|---|---|
| Day 0 | Placement |
| Day 7 | Callused |
| Day 10 | Callus, diameter 0.3 mm |
| Day 28 | Callus, diameter 0.8 mm |
| Day 35 | Callus, diameter 2.6 mm |

From these results, it was confirmed that, according to the culture apparatus of the present invention, the plant tissue can be grown similar to the conventional agar media, regardless of species of a plant and a tissue part, and plant hormones in a culture medium influence on morpholgenesis and propagation of a plant tissue via the microporous body. A callused rate of an anther of strawberry was 55.1%.

From this, it was demonstrated that a plant tissue can be cultured using the microporous body in the present culture apparatus as a medium, and the advantages can be sufficiently exerted without the disadvantages of the previous medium.

Culture Experiment 2

(1) Culture Apparatus

According to the same manner as that for the above culture experiment 1 expect that 130 ml of a modified Ohta culture medium (obtained by dissolving 10 g of glucose, 1 g of citric acid, 1 g of ammonium tartrate, 1 g of potassium phosphate, 1 g of magnesium sulfate, 50 mg of calcium chloride and 7 g of HEPES in 1 liter of water) as a culture medium was placed in the culture apparatus, an experiment was performed.

(2) Test Material

As test materials, filamentous fungi *Oospora roseoflava*, and *Flammulila velutipes* were used.

(3) Culture

Under the aseptic conditions, a petri dish was removed from the culture apparatus 2 the filamentous fungus was seeded on a central part of a bottom of the pan type part of the microporous body, with a platinum needle, and the pan type part was sealed with a petri dish again. The filamentous fungus seeded on the culture apparatus 2 like this was subjected to stationary culture at 26° C. under the natural sunshine conditions (around 10 cm beyond a frosted glass).

(4) Results (i) *Oospora Roseoflave*

Process of growth of *Oospora roseoflava* seeded on the culture apparatus 2 as described above is shown in Table 4 and FIGS. 18-21.

TABLE 4

| Hours after seeding | Process in growth of filamentous fungus |
|---|---|
| 0 hour | Seeding |
| 26 hours | Flora, diameter 5.2 mm |
| 49 hours | Flora, diameter 29.6 mm |
| 73 hours | Flora, diameter 56.8 mm |
| 91 hours | Flora, diameter 56.8 mm (Bottom 22.9 mm, Inner side 5.1 mm) |

(ii) *Flammulina Velutipes*

Process of growth of hypha of *Flammulina velutipes* seeded on the culture apparatus 2 as described above is shown in Table 5 and FIGS. 22-26.

TABLE 5

| Time after seeding | |
|---|---|
| 0 hour | Seeding |
| Day 10 | Flora, diameter 19.6 mm |
| Day 11 | Flora, diameter 34.6 mm |
| Day 12 | Flora, diameter 42.0 mm |
| Day 13 | Flora, diameter 44.8 mm |
| Day 14 | Flora, diameter 54.0 mm |
| Day 15 | Flora, diameter 56.0 mm |

From these results, it was confirmed that fungi can be grown by the present culture apparatus regardless of a kind of a fungus.

Culture Experiment 3

(1) Culture Apparatus

According to the same manner as that for the above culture experiment 1 except that 130 ml of a potato-sucrose culture medium (obtained by placing 200 g of a potato, a skin of which had been peeled considerably, in an appropriate amount of water, boiling for 30 minutes, filtrating it, adding 10 g of sucrose and water to adjusted to 1 liter with water) as a culture medium was placed in the culture apparatus 2, an experiment was performed.

(2) Test Material

As a test material, a bacterium *Bacillus subtilis* was used.

(3) Culture

Under the aseptic conditions, a petri dish was removed from the culture apparatus 2 a *Bacillus subtilis* suspension was coated on a bottom of a pan type part of a microporous body, and the pan type part was sealed with the petri dish again. The bacterium seeded on the culture apparatus 2 like this was subjected to stationary culture at 26° C. under the natural sunshine conditions (around 10 cm beyond a frosted glass).

(4) Results

Figure 27:
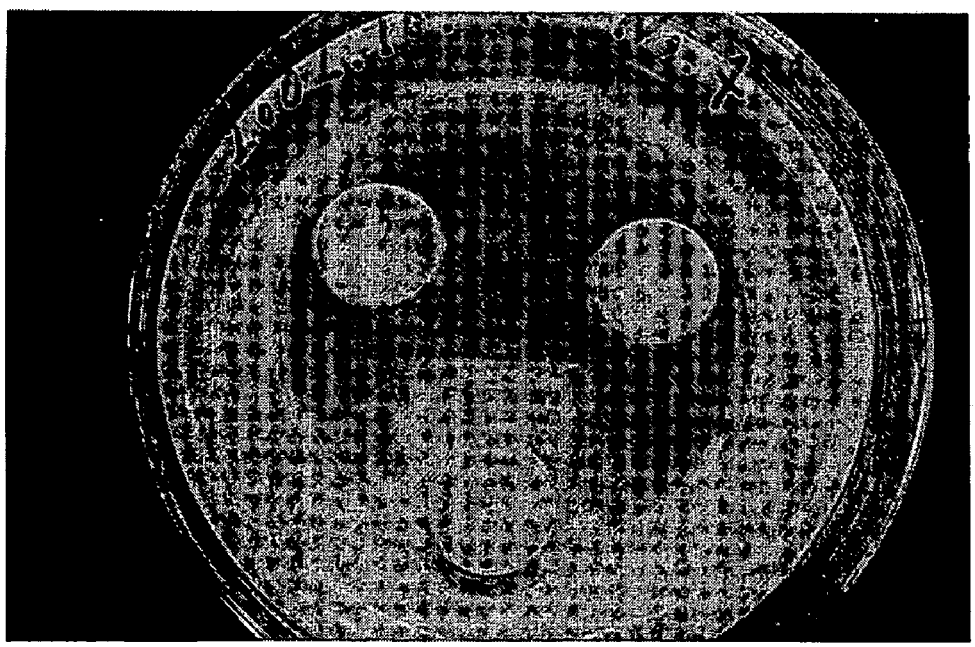
FIG. 27 is a photograph as a substitute for a drawing showing a bacterial flora of bacterium *Bacillus subtilis* at 66 hours after inoculated on the culture apparatus 2 of the present invention.
Figure 28:
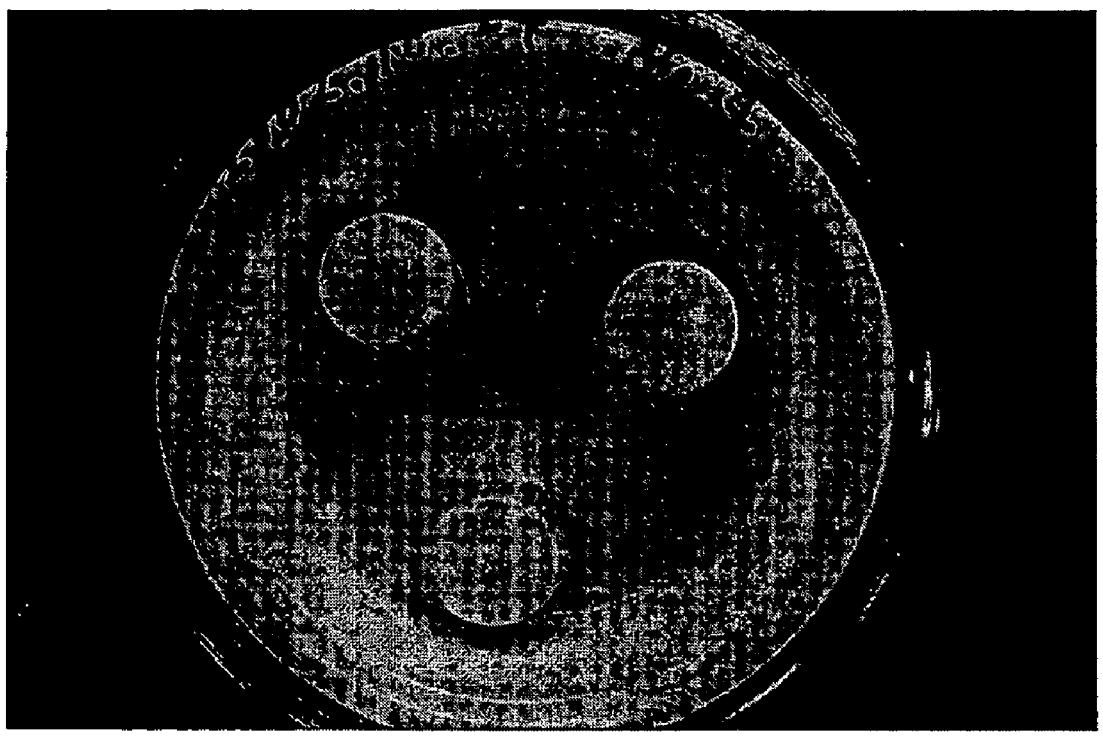
FIG. 28 is a photograph as a substitute for a drawing showing a bacterial flora of bacterium *Bacillus subtilis* at 109 hours after inoculated on the culture apparatus 2 of the present invention.

The appearance of growth of *Bacillus subtilis* seeded on the culture apparatus 2 as described above is shown in FIGS. 27 and 28, and process of growth for 1 flora is shown in Table 6.

TABLE 6

| Time after seeding | Process of growth of bacterium |
|---|---|
| 0 hour | Seeding |
| 66 hours | Flora, diameter 2.00 mm |
| 92 hours | Flora, diameter 5.29 mm |
| 109 hours | Flora, diameter 5.94 mm |
| 118 hours | Flora, diameter 7.12 mm |
| 132 hours | Flora, diameter 7.74 mm |

From this result, it was confirmed that bacteria can be also grown by the present culture apparatus.

Contamination Inhibiting Experiment

Figure 29:
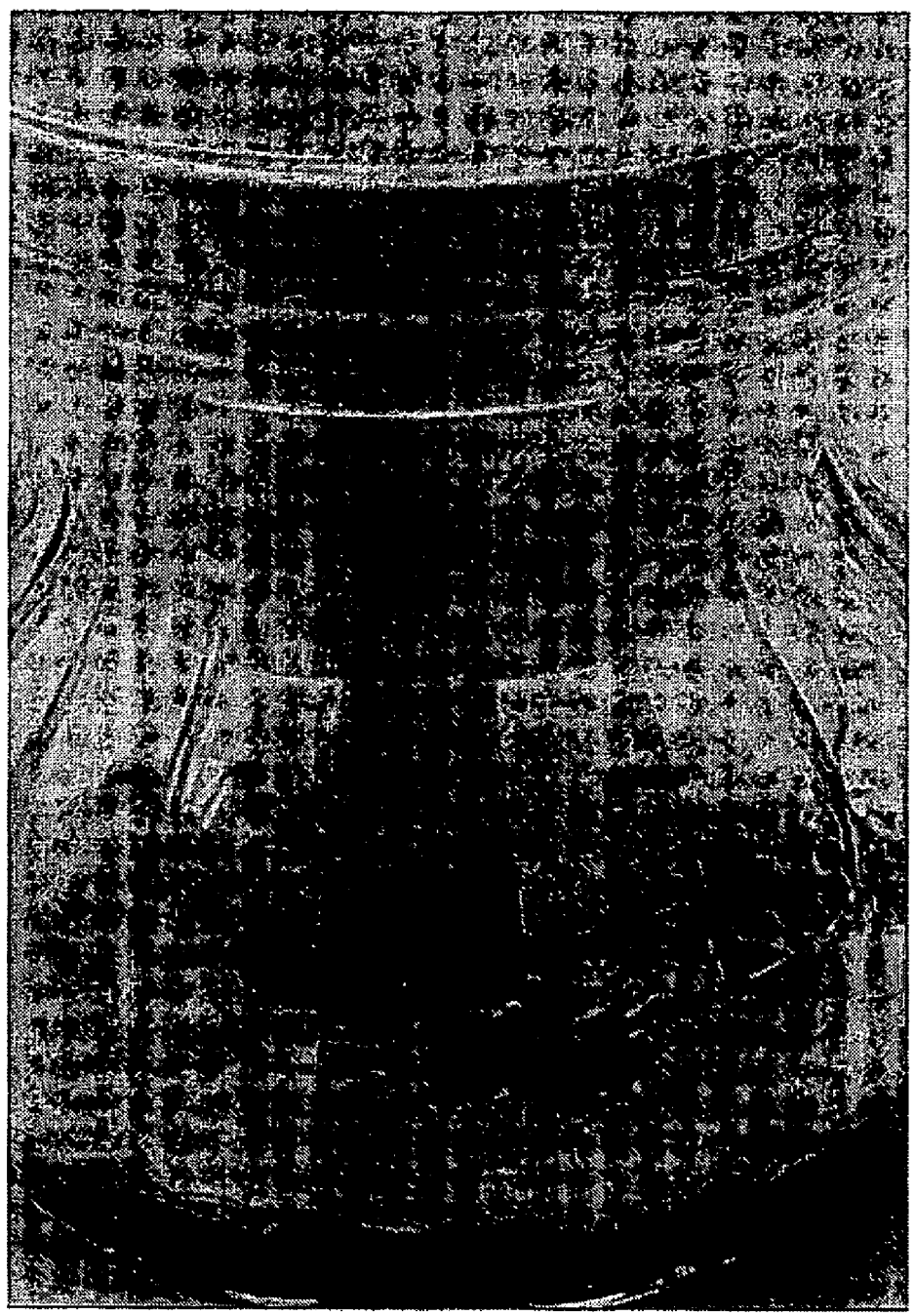
FIG. 29 is a photograph as a substitute for a drawing showing a fungus flora of *Gonytrichum macrocladum* on the day 55 after seeded on the culture apparatus 2 of the present invention.
Figure 30:
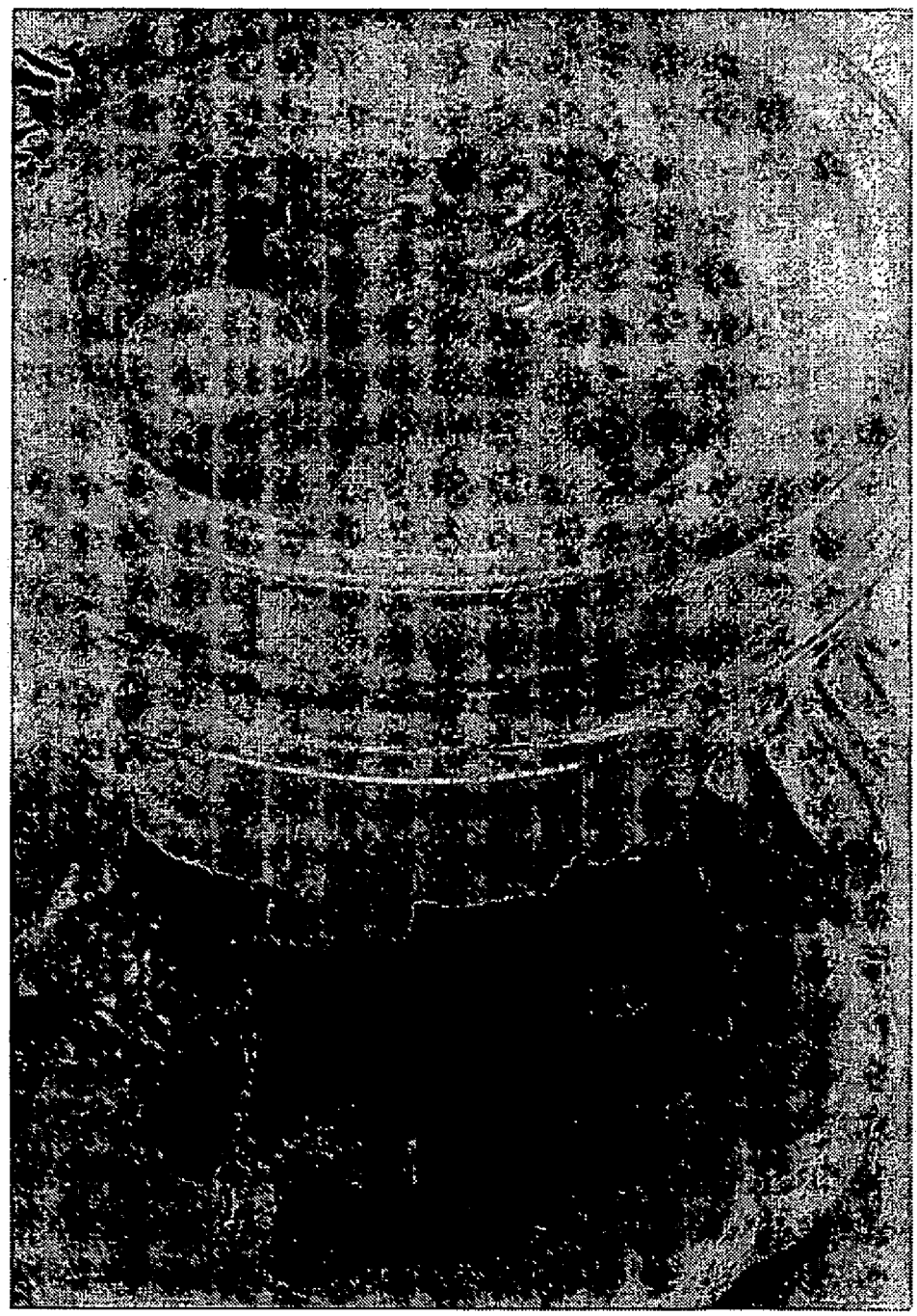
FIG. 30 is a photograph as a substitute for a drawing showing a fungus flora of Gonytrichum macrocladum on the day 55 after seeded on the culture apparatus 2 of the present invention.

A filamentous fungus, *Gonytrichum macrocladum* was seeded on a culture medium of the culture apparatus 2 used in the above culture experiment for strawberry anther, and subjected to stationary culture at 26° C. under the natural sunshine conditions (around 10 cm beyond a frosted glass). The results are shown in FIGS. 29 and 30.

As apparent from these figures, growth and elongation of a filamentous fungus seeded on a culture medium are inhibited at a lower part of the pillar type part of the microporous body even 55 days after seeding, and the fungus does not reach the pan type part where an organism tissue is being cultured. From this result, it was confirmed that, according to the culture apparatus of the present invention, even when a pooled culture medium is contaminated with a filamentous fungus, invasion of a filamentous fungus is inhibited or suppressed due to the filtering effects of the microporous body between the culture medium and an organism sample, and an organism sample can be transferred to another culture apparatus before contaminated and, thereby, the sample can be continued to be cultured again.

INDUSTRIAL APPLICABILITY

According to the present invention, there is provided a culture apparatus in which only a small amount of a culture medium is consumed, a necessity of operations such as stirring and shaking are reduced, the number of necessary subculture can be reduced and, thereby, culturing of an organism tissue or an organism cell over a longer period becomes possible without subculture operation so the culture apparatus can be provided by which a greater amount of useful substance can be obtained more conveniently in a single culture operation, upon extraction of useful substance from a tissue or cell. And contamination upon subculture operation and other stimulation having adverse influences (physical stimulation upon subculturing) can be prevented. In addition, culturing which is not influenced by a pH of a culture medium and a culturing temperature or the like becomes possible. In addition, thinner, smaller, lighter culture apparatus can be provided.

What is claimed is:

1. A method of in vitro culturing an organism tissue or cell, which comprising the following steps:
    placing a culture medium and a microporous body into a container such that only a part of the microporous body is immersed in the culture medium, wherein the microporous body has communicating pores having a pore diameter of 0.02-20 μm;
    placing the organism tissue or cell to be cultured on a surface of the microporous body where the culture medium has been transferred upwardly via communicating pores in the interior of the microporous body having the capillary attraction;
    allowing the organism tissue or cell to absorb the culture medium from the surface of the microporous body;
    growing the organism tissue or cell inside the container, wherein the culture medium, the microporous body, the container, and a lid or a plug for the container are sterile prior to placing the organism tissue or cell on the surface of the microporous body under aseptic conditions, the container is covered with the lid or the plug under aseptic conditions after placing the organism tissue or cell inside, the container is covered with the lid or the plug during culturing, and gases and/or medium optionally added to the container after placing the organism tissue or cell inside are sterile and introduced under aseptic conditions.

2. The method of in vitro culturing an organism tissue or cell according to claim 1, wherein the organism tissue or cell is a tissue or a cell of plants, fungi or bacteria.

3. The method of in vitro culturing an organism tissue or cell according to claim 1, wherein the microporous body has a shape of an upright cylindrical or pillar type.

4. The method of in vitro culturing an organism or cell according to claim 1, wherein the microporous body comprises a cylindrical or pillar type part, and a pan type part continuing upwardly from the cylindrical or pillar type part and having a greater outer diameter than that of the cylindrical or pillar type part, in which a center of the pan type part is recessed, wherein a part of the pan type part is projected in its diametric direction and has a greater outer diameter than that of an opening of a container, and the microporous body is supported by the container by contact between a bottom of the projected part and a periphery of the opening of the container.

5. The method of in vitro culturing an organism tissue or cell according to claim 1, wherein the microporous body is a fired product of a non-metal inorganic solid material.

6. The method of in vitro culturing an organism tissue or cell according to claim 1, wherein the organism tissue or cell is from a plant and the culture medium is a dedifferentiation culture medium, a differentiation culture medium, a regeneration culture medium, a preservation culture medium, a selection culture medium, an isolation culture medium or a cross culture medium.

7. The method of in vitro culturing an organism tissue or cell according to claim 1, wherein the organism tissue or cell is from a plant and the culture medium is a dedifferentiation culture medium.

8. The method of in vitro culturing an organism tissue or cell according to claim 1, wherein plant tissue is cultured and the plant tissue is sterilization-treated before being placed on the surface of the microporous body.

9. The method of in vitro culturing an organism tissue or cell according to claim 1, wherein the lid or the plug has an aperture for introducing a gas.

10. The method of in vitro culturing an organism tissue or cell according to claim 1, wherein the lid or the plug is threaded and the container is threaded and the lid or the plug can be screwed onto the container to close the container.

11. The method of in vitro culturing an organism tissue or cell according to claim 1, wherein each of the culture medium, the microporous body, the container, and the lid or the plug are sterilized by autoclaving, dry heat sterilization, or ultraviolet ray sterilization, or gamma ray sterilization.

12. The method of in vitro culturing an organism tissue or cell according to claim 1, wherein the microporous body has communicating pores having a pore diameter of 0.2-3 μm.

13. The method of in vitro culturing an organism tissue or cell according to claim 1, wherein the microporous body is capable of retaining water at 0.05 to 5 wt water/wt microporous body at a temperature of 20° C.

* * * * *